United States Patent
Jones et al.

(10) Patent No.: US 12,270,072 B2
(45) Date of Patent: Apr. 8, 2025

(54) RAPID THERMOCYCLING METHODS

(71) Applicant: Biofire Diagnostics, LLC, Salt Lake City, UT (US)

(72) Inventors: Charles Jones, Salt Lake City, UT (US); Andrew Hemmert, Murray, UT (US); Robert Crisp, Cottonwood Heights, UT (US); Elizabeth Diana Campbell, West Valley City, UT (US); Karina S. Kirk, Salt Lake City, UT (US); Andrew Carter Hatch, West Jordan, UT (US)

(73) Assignee: BioFire Diagnostics, LLC, Salt Lake City, UT (US)

( * ) Notice: Subject to any disclaimer, the term of this patent is extended or adjusted under 35 U.S.C. 154(b) by 0 days.

(21) Appl. No.: 16/631,395

(22) PCT Filed: Jun. 7, 2019

(86) PCT No.: PCT/US2019/036016
§ 371 (c)(1),
(2) Date: Jan. 15, 2020

(87) PCT Pub. No.: WO2019/236978
PCT Pub. Date: Dec. 12, 2019

(65) Prior Publication Data
US 2020/0385781 A1 Dec. 10, 2020
US 2021/0123089 A9 Apr. 29, 2021

Related U.S. Application Data

(60) Provisional application No. 62/681,830, filed on Jun. 7, 2018.

(51) Int. Cl.
*C12Q 1/68* (2018.01)
*C12Q 1/686* (2018.01)

(52) U.S. Cl.
CPC .................. *C12Q 1/686* (2013.01)

(58) Field of Classification Search
CPC .................................... C12Q 1/686
See application file for complete search history.

(56) References Cited

U.S. PATENT DOCUMENTS

| | | |
|---|---|---|
| 5,705,366 A | 1/1998 | Backus |
| 6,251,638 B1 | 6/2001 | Umansky et al. |
| 6,261,431 B1 * | 7/2001 | Mathies ........... G01N 27/44743 |
| | | 204/600 |
| 8,895,295 B2 | 11/2014 | Ririe et al. |
| 10,465,239 B2 | 11/2019 | Li |
| 2006/0110763 A1 | 5/2006 | Kopp |
| 2010/0056383 A1 * | 3/2010 | Ririe ................ G01N 33/54386 |
| | | 506/7 |
| 2015/0118715 A1 * | 4/2015 | Wittwer .................... B01L 7/02 |
| | | 435/194 |
| 2017/0297028 A1 | 10/2017 | Jones et al. |

FOREIGN PATENT DOCUMENTS

| | | | |
|---|---|---|---|
| WO | 2017/147085 | 8/2017 | |
| WO | WO-2017147085 A1 * | 8/2017 | ............. C12Q 1/686 |

OTHER PUBLICATIONS

Applied Biosystems, "Thermal Cyclers: Key Thermal Cycling Concepts and Ramp Rates," Apr. 22, 2015.
International Search Report and Written Opinion, PCT/US2019/036016, Oct. 4, 2019.
Fischer-Romero C. et al: "Development and evaluation of a broad-range PCR-ELISA assay with Borrelia burgdorferi and *Streptococcus pneumoniae* as model organisms for reactive arthritis and bacterial meningitis", Advances in Biomagnetism, 7th Conference Aug. 13-18, 1989, New York, New York, NY, US, vol. 40, No. 1, Mar. 1, 2000 (Mar. 1, 2000), pp. 79-88, XP002214163.
Supplementary European Search Report issued by the European Patent Office for European Patent Application No. 19815055.9, mailed on Feb. 9, 2022; 8 pages.

* cited by examiner

*Primary Examiner* — Stephanie K Mummert
*Assistant Examiner* — Olayinka A Oyeyemi
(74) *Attorney, Agent, or Firm* — Kenneth E. Horton; Barnes & Thornburg LLP

(57) ABSTRACT

Instruments, methods, and kits are disclosed for performing fast thermocycling.

26 Claims, 17 Drawing Sheets

RAPID THERMOCYCLING METHODS

CROSS REFERENCE TO RELATED APPLICATIONS

This application claims the benefit of and priority to U.S. Provisional Patent Application No. 62/681,830 filed Jun. 7, 2018, the entirety of which is incorporated herein by reference.

BACKGROUND

1. Technical Field

Embodiments of the present disclosure relate generally to methods and devices for amplifying nucleic acids.

2. Background

In the United States, Canada, and Western Europe infectious disease accounts for approximately 7% of human mortality, while in developing regions infectious disease accounts for over 40% of human mortality. Infectious diseases lead to a variety of clinical manifestations. Among common overt manifestations are fever, pneumonia, meningitis, diarrhea, and diarrhea containing blood. While the physical manifestations suggest some pathogens and eliminate others as the etiological agent, a variety of potential causative agents remain, and clear diagnosis often requires a variety of assays be performed. Traditional microbiology techniques for diagnosing pathogens can take days or weeks, often delaying a proper course of treatment.

In recent years, the polymerase chain reaction (PCR) has become a method of choice for rapid diagnosis of infectious agents. PCR can be a rapid, sensitive, and specific tool to diagnose infectious disease. A challenge to using PCR as a primary means of diagnosis is the variety of possible causative organisms or viruses and the low levels of organism or virus present in some pathological specimens. It is often impractical to run large panels of PCR assays, one for each possible causative organism or viruses, most of which are expected to be negative. The problem may be exacerbated when pathogen nucleic acid is at low concentration and requires a large volume of sample to gather adequate reaction templates. In some cases, there is inadequate sample to assay for all possible etiological agents. A solution is to run "multiplex PCR" wherein the sample is concurrently assayed for multiple targets in a single reaction. While multiplex PCR has proven to be valuable in some systems, shortcomings exist concerning robustness of high level multiplex reactions and difficulties for clear analysis of multiple products. To solve these problems, the assay may be subsequently divided into multiple secondary PCRs. Nesting secondary reactions within the primary product increases robustness. Closed systems such as the FilmArray® (BioFire Diagnostics, LLC, Salt Lake City, UT) reduce handling, thereby diminishing contamination risk.

PCR may be conceptually divided into 3 reactions, each usually assumed to occur over time at each of three temperatures. Such an "equilibrium paradigm" of PCR is easy to understand in terms of three reactions (denaturation, annealing, and extension) occurring at 3 temperatures over 3 time periods each cycle. However, this equilibrium paradigm does not fit well with physical reality. Instantaneous temperature changes do not occur; it takes time to change the sample temperature, and temperature may not be homogeneous throughout the sample, particularly where larger volumes are used. Furthermore, individual reaction rates vary with temperature, and once primer annealing occurs, polymerase extension immediately follows. More accurate, particularly for rapid PCR, is a kinetic paradigm where reaction rates and temperature are always changing. Holding the temperature constant during PCR is not necessary as long as the products denature and the primers anneal. Under the kinetic paradigm of PCR, product denaturation, primer annealing, and polymerase extension may temporally overlap and their rates continuously vary with temperature. Under the equilibrium paradigm, a cycle is defined by 3 temperatures each held for a time period, whereas the kinetic paradigm requires transition rates and target temperatures. Illustrative time/temperature profiles for the equilibrium and kinetic paradigms are shown in FIGS. 5a-5b. However, it is understood that these temperature profiles are illustrative only and that in some implementations of PCR, the annealing and extension steps are combined so that only 2 temperatures are needed.

When PCR was first popularized in the late 1980s, the process was slow. A typical protocol was one minute for denaturation at 94° C., two minutes for annealing at 55° C., and three minutes for extension at 72° C. When the time for transition between temperatures was included, 8 minute cycles were typical, resulting in completion of 30 cycles in four hours. Twenty-five percent of the cycling time was spent in temperature transitions. As cycling speeds increased, the proportion of time spent in temperature transitions also increased and the kinetic paradigm became more and more relevant. During rapid cycle PCR, the temperature is usually changing. For rapid cycle PCR of short products (<100 bps), 100% of the time may be spent in temperature transition and no holding times are necessary. For rapid cycle PCR of longer products, a temperature hold at an optimal extension temperature may be included.

In isolation, the term "rapid PCR" is both relative and vague. A one-hour PCR is rapid compared to four hours, but slow compared to 15 minutes. Furthermore, PCR protocols can be made shorter if one starts with higher template concentrations or uses fewer cycles. A more specific measure is the time required for each cycle. Thus, "rapid cycle PCR" (or "rapid cycling") was defined in 1994 as 30 cycles completed in 10-30 minutes, resulting in cycles of 20-60 seconds each. This actual time of each cycle is longer than the sum of the times often programmed for denaturation, annealing and extension, as time is needed to ramp the temperatures between each of these stages. Initial work in the early 1990s established the feasibility of rapid cycling using capillary tubes and hot air for temperature control. Over the years, systems have become faster, and the kinetic requirements of denaturation, annealing, and extension have become clearer.

Rapid protocols use momentary or "0" second holds at the denaturation and annealing temperatures. That is, the temperature-time profiles show temperature spikes for denaturation and annealing, without holding the top and bottom temperatures. Denaturation and annealing can occur very quickly.

Conclusions from this early work were: 1) denaturation of PCR products is very rapid with no need to hold the denaturation temperature, 2) annealing of primers can occur very quickly, particularly with higher primer concentrations, and annealing temperature holds may not be necessary, and 3) the required extension time depends on PCR product length and polymerase concentration. Also, rapid cycle PCR is not only faster, but better in terms of specificity and yield as long as the temperature was controlled precisely.

One way to decrease cycle time is to introduce variations to the PCR protocol to ease the temperature cycling requirements. Longer primers with higher Tms allow higher annealing temperatures. By limiting the product length and its Tm, denaturation temperatures can be lowered to just above the product Tm. In combination, higher annealing and lower denaturation temperatures decrease the temperature range required for successful amplification. Reducing 3-step cycling (denaturation, annealing, and extension) to 2-steps (denaturation and a combined annealing/extension step) also simplifies the temperature cycling requirements. Two-step cycling can, however, compromise polymerase extension rates if the combined annealing/extension step is performed at temperatures lower than the 70 to 80° C. temperature optimum where the polymerase is most active, particularly with fast ramp rates. Polymerase extension rates are log-linear with temperature until about 70-80° C., with a reported maximum of 60-120 bp/s.

Even with protocol variations, amplification efficiency and yield are often poor when cycle times are <20 seconds when compared to control reactions. These efforts towards faster PCR appear dominated by engineering with little focus on the biochemistry. As cycle times decrease from 20 seconds towards 2 seconds, PCR yield decreases and finally disappears, reflecting a lack of robustness even with simple targets at high copy number.

Recently, a system has been reported using thin walled capillaries and water baths to thermocycle or using induction heating (U.S. Pat. No. 9,932,634; US 2016-0289736, herein incorporated in their entireties by reference) at speeds of less than 10 seconds per cycle, and in some embodiments less than one second per cycle. Adjustments in chemistry for this "extreme PCR", wherein polymerase and primer concentration are increased, permit the polymerase chain reaction to proceed at such fast rates.

In one example of extreme PCR, the polymerase is provided at a concentration of at least 0.5 µM and primers are each provided at a concentration of at least 2 µM, and in some examples the primer concentration is 2.5 µM or more. By non-limiting example, annealing time may be defined by annealing time=k1/[primer], wherein k1 is a constant and [primer] is the concentration of each primer, and time at the elongation temperature may be defined by elongation time=k2(extension length)/([polymerase]*(polymerase speed)), wherein k2 is a proportionality constant, [polymerase] is the concentration of the polymerase, and polymerase speed is a rate of polymerase incorporation of bases in nucleotides. In another example of extreme PCR, the polymerase to primer ratio is illustratively (about 0.03 to about 0.4 polymerase):(total primer concentration), and the polymerase concentration is at least 0.5 µM. It is noted that polymerase Unit definitions can be confusing. For native Taq polymerase, 0.4 U/10 µl is about 1.5 nM under typical rapid cycling conditions.

While improvements in chemistry are reported in U.S. Pat. No. 9,932,634, the illustrative device uses large water baths, and it is ideally placed inside a water-resistant cabinet. Rapid temperature cycling having cycle times of 20 seconds or less using the chemistry of U.S. Pat. No. 9,932,634 in commercial instrumentation would be desired. While performing two-step thermocycling in a closed container, one can rapidly thermocycle the small individual second-stage reactions, but it is much more difficult to thermocycle the large volume of the first-stage reaction fast enough to take advantage of the chemistries of U.S. Pat. No. 9,932,634.

The present application relates to fast PCR, including devices, kits, and methods for fast PCR, illustratively with altered cycling parameters, particularly during the first few cycles when hardware and/or reaction components are provided below PCR temperatures.

BRIEF SUMMARY

Described herein are devices (instruments and systems) and methods for rapid amplification of nucleic acids in an amplification container. In an illustrative embodiment, methods for performing PCR are provided, the methods comprising thermocycling a PCR mixture having a first volume in an amplification container for a first number of cycles, each of the first number of cycles comprising a first cycle time, a first annealing temperature, a first annealing hold, a first denaturation temperature, and a first denaturation hold, reducing the volume of the PCR mixture in the amplification container to a second volume, the second volume being smaller than the first volume, and thermocycling the second volume of PCR mixture in at least a portion of the amplification container for a second number of cycles, each of the second number of cycles comprising a second cycle time, a second annealing temperature, a second annealing hold, a second denaturation temperature, and a second denaturation hold, the second cycle time being shorter than the first cycle time and the second denaturation temperature being lower than the first denaturation temperature.

In another aspect, methods for performing PCR are described, the methods comprising thermocycling a PCR mixture with a first volume in an amplification container for at least a first cycle, the first cycle comprising a first cycle time, a first annealing temperature, a first annealing hold, a first denaturation temperature, and a first denaturation hold, thermocycling for a second number of cycles, each of the second number of cycles comprising a second cycle time, a second annealing temperature, a second annealing hold, a second denaturation temperature, and a second denaturation hold, wherein at least one of the first cycle time, the first annealing temperature, the first annealing hold, and the first denaturation temperature differs from the corresponding one of the second cycle time, the second annealing temperature, the second annealing hold, the second denaturation temperature, and the second denaturation hold, reducing the volume of the PCR mixture in the amplification container to a second volume, the second volume being smaller than the first volume, and thermocycling for a third number of cycles, each of the third number of cycles comprising a third cycle time, a third annealing temperature, a third annealing hold, a third denaturation temperature, and a third denaturation hold, wherein at least one of the second cycle time, the second annealing temperature, the second annealing hold, the second denaturation temperature differs from the corresponding one of the third cycle time, the third annealing temperature, the third annealing hold, the third denaturation temperature, and the third denaturation hold.

In yet another aspect, methods for performing PCR are described, the method comprising thermocycling a PCR mixture with a first volume in an amplification container for a first number of cycles, each of the first number of cycles comprising a first cycle time, a first annealing temperature, a first annealing hold, a first denaturation temperature, and a first denaturation hold, reducing the volume of the PCR mixture in the amplification container to a second volume, the second volume being smaller than the first volume, and thermocycling the second volume of PCR mixture in at least a portion of the amplification container for a second number of cycles, each of the second number of cycles comprising a second cycle time, a second annealing temperature, a second annealing hold, a second denaturation temperature, and a second denaturation hold, the second cycle time being shorter than the first cycle time and one of the second denaturation temperature or second denaturation hold being lower than the first denaturation temperature or first denaturation hold.

Described herein are:

A1. A method for performing PCR, comprising
thermocycling a PCR mixture having a first volume in an amplification container for a first number of cycles, each of the first number of cycles comprising a first cycle time, a first annealing temperature, a first annealing hold, a first denaturation temperature, and a first denaturation hold,
reducing the volume of the PCR mixture in the amplification container to a second volume, the second volume being smaller than the first volume, and
thermocycling the second volume of PCR mixture in at least a portion of the amplification container for a second number of cycles, each of the second number of cycles comprising a second cycle time, a second annealing temperature, a second annealing hold, a second denaturation temperature, and a second denaturation hold, the second cycle time being shorter than the first cycle time and the second denaturation temperature being lower than the first denaturation temperature.

A2. The method of one or more of clauses A1, B1, or C1, wherein the first denaturation hold is longer than the second denaturation hold.

A3. The method of one or more of clauses A1, A2, B1, or C1, wherein the first annealing hold is longer than the second annealing hold.

A4. The method of one or more of clauses A1-A3, B1, or C1, wherein the amplification container is compressible, and reducing the volume of the PCR mixture is performed by expelling a portion of the sample from the amplification container.

A5. The method of one or more of clauses A1-A4, B1, or C1, wherein the amplification container is in contact with at least two temperature zones, and at least one of the thermocycling processes includes moving the sample between the temperature zones.

A6. The method of one or more of clauses A1-A5, B1, or C1, wherein the amplification container is heated by a heater that thermocycles between several temperatures.

A7. The method of one or more of clauses A1-A6, B1, or C1, wherein the first number of cycles has a first ramp rate and the second number of cycles has a second ramp rate, wherein the second ramp rate is faster than the first ramp rate.

A8. The method of one or more of clauses A1-A7, B1, or C1, further comprising reducing the volume of the PCR mixture in the amplification container to a third volume, the third volume being smaller than the second volume, and thermocycling the third volume of PCR mixture in at least a portion of the amplification container for a third number of cycles, each of the third number of cycles having a third cycle time, the third cycle time being shorter than the second cycle time.

A9. The method of clause A8, wherein the first number of cycles has a first ramp rate, the second number of cycles has a second ramp rate, and the third number of cycles has a third ramp rate, wherein the third ramp rate is faster than the second ramp rate, and the second ramp rate is faster than the first ramp rate.

A10. The method of one or more of clauses A1-A9, B1, or C1, further comprising performing an initial cycle prior to thermocycling for a first number of cycles, the initial cycle comprising an initial cycle time, an initial annealing temperature, an initial denaturation temperature, and an initial denaturation hold, wherein the initial denaturation hold is longer than the first denaturation hold, and the initial denaturation temperature is lower than the first denaturation temperature.

A11. The method of one or more of clauses A1-A10, B1, or C1, wherein the first volume of PCR mixture in the amplification container with is thermocycled in an amplification zone of an instrument, and the method further comprises preheating the amplification zone prior to placing the first volume of PCR mixture in the amplification zone.

A12. The method one or more of clauses A1-A11, B1, or C1, wherein the first volume of PCR mixture in the amplification container is thermocycled in an amplification zone of an instrument, the amplification zone heated by one or more heaters, further comprising reducing a thermal mass of the one or more heaters contemporaneous with or subsequent to reducing the volume of the PCR mixture to the second volume.

A13. The method of one or more of clauses A1-A12, B1, or C1, further comprising forming the first volume of PCR mixture by mixing a sample comprising nucleic acids with a PCR master mix, wherein the PCR master mix is heated above the first annealing temperature prior to mixing.

A14. The method of one or more of clauses A1-A12, B1, or C1, wherein the sample is heated to at least 50° C. prior to mixing the sample with the PCR master mix.

A15. The method of one or more of clauses A1-A14, B1, or C1, wherein the amplification container comprises a single reaction container and both thermocycling processes take place in that reaction container.

A16. The method of one or more of clauses A1-A14, B1, or C1, wherein the amplification container includes two blisters and both thermocycling processes take place in both blisters.

A17. The method of one or more of clauses A1-A14, B1, or C1, wherein the amplification container includes two blisters, wherein thermocyling the first volume of PCR mixture takes place in both of the two blisters, and wherein thermocyling the second volume of PCR mixture takes place in only one of the two blisters.

A18. The method of one or more of clauses A1-A17, B1, or C1, wherein no additional reaction components are added between the thermocycling processes.

B1. A method for performing PCR, comprising
thermocycling a PCR mixture with a first volume in an amplification container for at least a first cycle, the first cycle comprising a first cycle time, a first annealing temperature, a first annealing hold, a first denaturation temperature, and a first denaturation hold,
thermocycling for a second number of cycles, each of the second number of cycles comprising a second cycle time, a second annealing temperature, a second annealing hold, a second denaturation temperature, and a second denaturation hold, wherein at least one of the first cycle time, the first annealing temperature, the first annealing hold, and the first denaturation temperature differs from the corresponding one of the second cycle time, the second annealing temperature, the second annealing hold, the second denaturation temperature, and the second denaturation hold, reducing the volume of the PCR mixture in the amplification container to a second volume, the second volume being smaller than the first volume, and thermocycling for a third number of cycles, each of the third number of cycles comprising a third cycle time, a third annealing temperature, a third annealing hold, a third denaturation temperature, and a third denaturation hold, wherein at least one of the second cycle time, the second annealing temperature, the second annealing hold, the second denaturation temperature differs from the corresponding one of the third cycle time, the third annealing temperature, the third annealing hold, the third denaturation temperature, and the third denaturation hold.

B2. The method of clause B1, wherein the third cycle time is shorter than the second cycle time.

B3. The method of at least one of clause B1 or clause B2, wherein the third denaturation temperature is lower than the second denaturation temperature.

B4. The method of clause B2, wherein the first denaturation hold is longer than the second denaturation hold.

C1. A method for performing PCR, comprising thermocycling a PCR mixture with a first volume in an amplification container for a first number of cycles, each of the first number of cycles comprising a first cycle time, a first annealing temperature, a first annealing hold, a first denaturation temperature, and a first denaturation hold, reducing the volume of the PCR mixture in the amplification container to a second volume, the second volume being smaller than the first volume, and thermocycling the second volume of PCR mixture in at least a portion of the amplification container for a second number of cycles, each of the second number of cycles comprising a second cycle time, a second annealing temperature, a second annealing hold, a second denaturation temperature, and a second denaturation hold, the second cycle time being shorter than the first cycle time and one of the second denaturation temperature or second denaturation hold being lower than the first denaturation temperature or first denaturation hold.

Additional features and advantages will be set forth in the description which follows or may be learned by the practice of such embodiments. The features and advantages of such embodiments may be realized and obtained by means of the instruments and combinations particularly pointed out in the appended claims. These and other features will become more fully apparent from the following description and appended claims, or may be learned by the practice of such embodiments as set forth hereinafter.

BRIEF DESCRIPTION OF THE DRAWINGS

In order to describe the manner in which the above-recited and other advantages and features can be obtained, a more particular description briefly described above will be rendered by reference to specific embodiments thereof which are illustrated in the appended drawings. Understanding that these drawings depict only typical embodiments and are not therefore to be considered to be limiting of its scope, the embodiments will be described and explained with additional specificity and detail through the use of the accompanying drawings in which.

DETAILED DESCRIPTION

Figure 1:
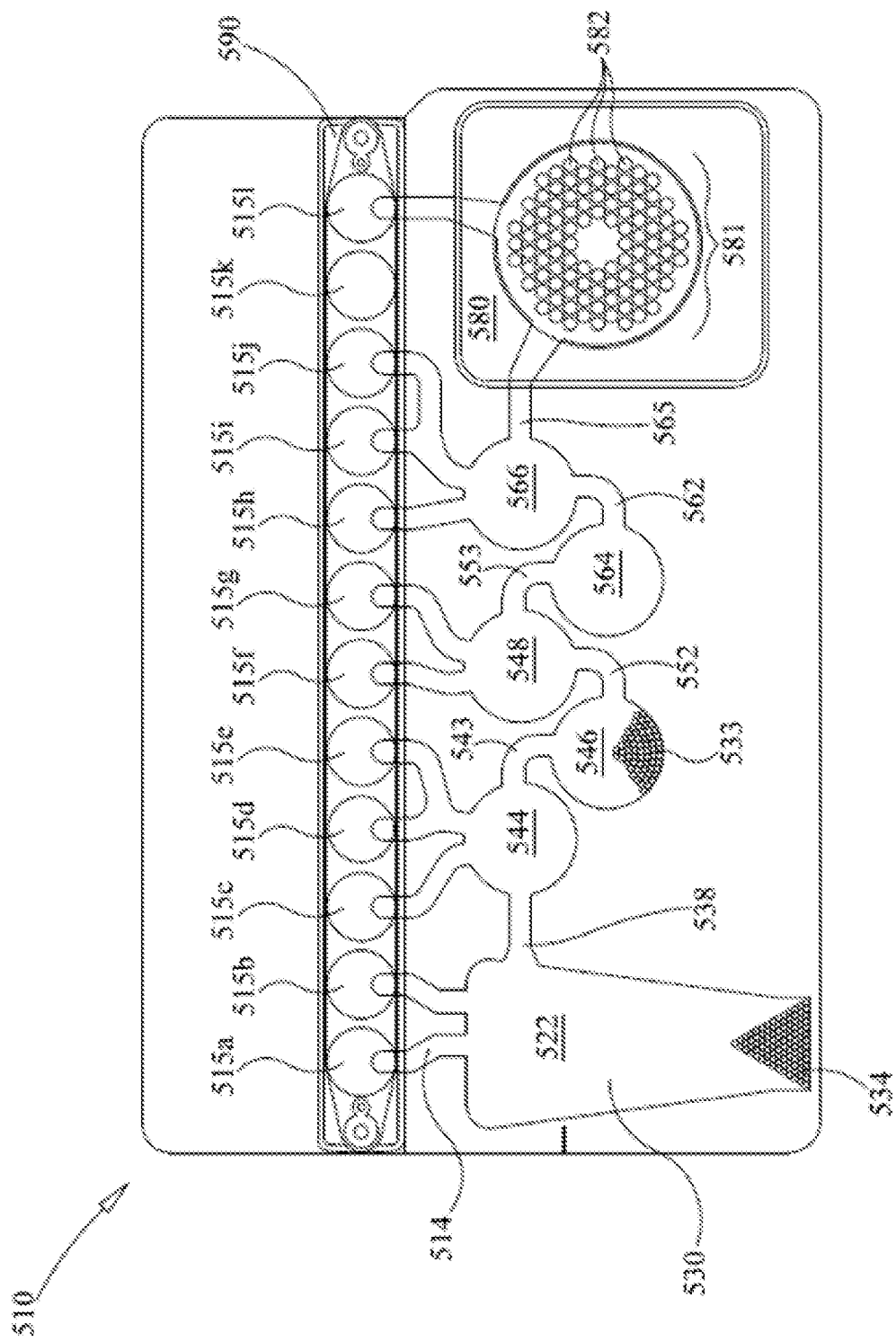
FIG. 1 shows a flexible pouch useful for self-contained PCR.

Example embodiments are described below with reference to the accompanying drawings. Many different forms and embodiments are possible without deviating from the spirit and teachings of this disclosure and so the disclosure should not be construed as limited to the example embodiments set forth herein. Rather, these example embodiments are provided so that this disclosure will be thorough and complete, and will convey the scope of the disclosure to those skilled in the art. In the drawings, the sizes and relative sizes of layers and regions may be exaggerated for clarity. Like reference numbers refer to like elements throughout the description.

Unless defined otherwise, all terms (including technical and scientific terms) used herein have the same meaning as commonly understood by one of ordinary skill in the art to which the present disclosure pertains. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description herein is for the purpose of describing particular embodiments only and is not intended to be limiting. While a number of methods and materials similar or equivalent to those described herein can be used in the practice of the present disclosure, only certain exemplary materials and methods are described herein.

All publications, patent applications, patents or other references mentioned herein are incorporated by reference in their entirety. In case of a conflict in terminology, the present specification is controlling.

Various aspects of the present disclosure, including devices, systems, methods, etc., may be illustrated with reference to one or more exemplary implementations. As used herein, the terms "exemplary" and "illustrative" mean "serving as an example, instance, or illustration," and should not necessarily be construed as preferred or advantageous over other implementations disclosed herein. In addition, reference to an "implementation" or "embodiment" of the present disclosure or invention includes a specific reference to one or more embodiments thereof, and vice versa, and is intended to provide illustrative examples without limiting the scope of the present disclosure, which is indicated by the appended claims rather than by the following description.

It will be noted that, as used in this specification and the appended claims, the singular forms "a," "an," and "the" include plural referents unless the content clearly dictates otherwise. Thus, for example, reference to "a tile" includes one, two, or more tiles. Similarly, reference to a plurality of referents should be interpreted as comprising a single referent and/or a plurality of referents unless the content and/or context clearly dictate otherwise. Thus, reference to "tiles" does not necessarily require a plurality of such tiles. Instead, it will be appreciated that independent of conjugation; one or more tiles are contemplated herein.

As used throughout this application the words "can" and "may" are used in a permissive sense (i.e., meaning having the potential to), rather than the mandatory sense (i.e., meaning must). Additionally, the terms "including," "having," "involving," "containing," "characterized by," variants thereof (e.g., "includes," "has," "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

As used herein, directional and/or arbitrary terms, such as "top," "bottom," "left," "right," "up," "down," "upper," "lower," "inner," "outer," "internal," "external," "interior," "exterior," "proximal," "distal," "forward," "reverse," and the like can be used solely to indicate relative directions and/or orientations and may not be otherwise intended to limit the scope of the disclosure, including the specification, invention, and/or claims.

It will be understood that when an element is referred to as being "coupled," "connected," or "responsive" to, or "on," another element, it can be directly coupled, connected, or responsive to, or on, the other element, or intervening elements may also be present. In contrast, when an element is referred to as being "directly coupled," "directly connected," or "directly responsive" to, or "directly on," another element, there are no intervening elements present.

Example embodiments of the present disclosure are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments of the present disclosure should not be construed as limited to the particular shapes of regions illustrated herein but are to include deviations in shapes that result, for example, from manufacturing. Accordingly, the regions illustrated in the figures are schematic in nature and their shapes are not intended to illustrate the actual shape of a region of a device and are not intended to limit the scope of exemplary embodiments.

It will be understood that although the terms "first," "second," etc. may be used herein to describe various elements, these elements should not be limited by these terms. These terms are only used to distinguish one element from another. Thus, a "first" element could be termed a "second" element without departing from the teachings of the present embodiments.

It is also understood that various implementations described herein can be utilized in combination with any other implementation described or disclosed, without departing from the scope of the present disclosure. Therefore, products, members, elements, devices, apparatuses, systems, methods, processes, compositions, and/or kits according to certain implementations of the present disclosure can include, incorporate, or otherwise comprise properties, features, components, members, elements, steps, and/or the like described in other implementations (including systems, methods, apparatus, and/or the like) disclosed herein without departing from the scope of the present disclosure. Thus, reference to a specific feature in relation to one implementation should not be construed as being limited to applications only within that implementation.

The headings used herein are for organizational purposes only and are not meant to be used to limit the scope of the description or the claims. To facilitate understanding, like reference numerals have been used, where possible, to designate like elements common to the figures. Furthermore, where possible, like numbering of elements have been used in various figures. Furthermore, alternative configurations of a particular element may each include separate letters appended to the element number.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The word "or" as used herein means any one member of a particular list and also includes any combination of members of that list.

The term "sample" includes an animal; a tissue or organ from an animal; a cell (either within a subject, taken directly from a subject, or a cell maintained in culture or from a cultured cell line); a cell lysate (or lysate fraction) or cell extract; a solution containing one or more molecules derived from a cell, cellular material, or viral material (e.g. a polypeptide or nucleic acid); or a solution containing a non-naturally occurring nucleic acid, which is assayed as described herein. A sample may also be any body fluid or excretion (for example, but not limited to, blood, urine, stool, saliva, tears, bile, or cerebrospinal fluid) that may or may not contain host or pathogen cells, cell components, or nucleic acids. Samples may also include environmental samples such as, but not limited to, soil, water (fresh water, waste water, etc.), air monitoring system samples (e.g., material captured in an air filter medium), surface swabs, and vectors (e.g., mosquitos, ticks, fleas, etc.).

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, mRNA, rRNA, cDNA, gDNA, ssDNA, dsDNA, or any combination thereof.

By "probe," "primer," or "oligonucleotide" is meant a single-stranded nucleic acid molecule of defined sequence that can base-pair to a second nucleic acid molecule that contains a complementary sequence (the "target"). The stability of the resulting hybrid depends upon the length, GC content, and the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes, primers, and oligonucleotides may be detectably-labeled, either radioactively, fluorescently, or non-radioactively, by methods well-known to those skilled in the art. dsDNA binding dyes may be used to detect dsDNA. It is understood that a "primer" is specifically configured to be extended by a polymerase, whereas a "probe" or "oligonucleotide" may or may not be so configured.

By "dsDNA binding dyes" is meant dyes that fluoresce differentially when bound to double-stranded DNA than when bound to single-stranded DNA or free in solution, usually by fluorescing more strongly. While reference is made to dsDNA binding dyes, it is understood that any suitable dye may be used herein, with some non-limiting illustrative dyes described in U.S. Pat. No. 7,387,887, herein incorporated by reference. Other signal producing substances may be used for detecting nucleic acid amplification and melting, illustratively enzymes, antibodies, etc., as are known in the art.

By "specifically hybridizes" is meant that a probe, primer, or oligonucleotide recognizes and physically interacts (that is, base-pairs) with a substantially complementary nucleic acid (for example, a sample nucleic acid) under high stringency conditions, and does not substantially base pair with other nucleic acids.

By "high stringency conditions" is meant typically to occur at about a melting temperature (Tm) minus 5° C. (i.e. 5° below the Tm of the probe). Functionally, high stringency conditions are used to identify nucleic acid sequences having at least 80% sequence identity.

While PCR is the amplification method used in the examples herein, it is understood that any amplification method that uses a primer may be suitable. Such suitable procedures include polymerase chain reaction (PCR); strand displacement amplification (SDA); nucleic acid sequence-based amplification (NASBA); cascade rolling circle amplification (CRCA), loop-mediated isothermal amplification of DNA (LAMP); isothermal and chimeric primer-initiated amplification of nucleic acids (ICAN); target based-helicase dependent amplification (HDA); transcription-mediated amplification (TMA), and the like. Therefore, when the term PCR is used, it should be understood to include other alternative amplification methods. For amplification methods without discrete cycles, reaction time may be used where measurements are made in cycles, doubling time, or crossing point (Cp), and additional reaction time may be added where additional PCR cycles are added in the embodiments described herein. It is understood that protocols may need to be adjusted accordingly. For examples using volume reduction, in illustrative examples, the volume is reduced after a suitable number of product molecules have been generated, either based on reaction time or cycle number.

While various examples herein reference human targets and human pathogens, these examples are illustrative only. Methods, kits, and devices described herein may be used to detect and sequence a wide variety of nucleic acid sequences from a wide variety of samples, including, human, veterinary, industrial, and environmental.

Various embodiments disclosed herein use a self-contained nucleic acid analysis pouch to assay a sample for the presence of various biological substances, illustratively antigens and nucleic acid sequences, illustratively in a single closed system. Such systems, including pouches and instruments for use with the pouches, are disclosed in more detail in U.S. Pat. Nos. 8,394,608; and 8,895,295; U.S. Patent Application Nos. 2014-0283945 and 2019-0046989; and PCT Publication No. WO2019/045807, herein incorporated by reference. However, it is understood that such pouches are illustrative only, and the nucleic acid preparation and amplification reactions discussed herein may be performed in any of a variety of open or closed system sample vessels as are known in the art, including 96-well plates, plates of other configurations, arrays, carousels, and the like, using a variety of nucleic acid purification and amplification systems, as are known in the art. While the terms "sample well", "amplification well", or the like are used herein, these terms are meant to encompass wells, tubes, and various other reaction containers, as are used in these amplification systems. In one embodiment, the pouch is used to assay for multiple pathogens. The pouch may include one or more blisters used as sample wells, illustratively in a closed system. Illustratively, various steps may be performed in the optionally disposable pouch, including nucleic acid preparation, primary large volume multiplex PCR, dilution of primary amplification product, and secondary PCR, culminating with optional real-time detection or post-amplification analysis such as melting-curve analysis. Further, it is understood that while the various steps may be performed in pouches, one or more of the steps may be omitted for certain uses, and the pouch configuration may be altered accordingly. In embodiments using volume reduction methods, the term "amplification container" is the portion of a sample vessel where amplification occurs. An amplification container may be a sample well or blister, or may be a combination of multiple sample wells or blisters that may be interconnected. In various illustrative embodiments described herein, amplification both before and after volume reduction may be performed in the same amplification container, although a portion of the amplification container may be used after volume reduction in certain embodiments.

FIG. 1 shows an illustrative pouch 510 that may be used in various embodiments, or may be reconfigured for various embodiments. Pouch 510 is similar to FIG. 15 of U.S. Pat. No. 8,895,295, with like items numbered the same. Fitment 590 is provided with entry channels 515a through 515l, which also serve as reagent reservoirs or waste reservoirs. Illustratively, reagents may be freeze dried in fitment 590 and rehydrated prior to use. Blisters 522, 544, 546, 548, 564, and 566, with their respective channels 514, 538, 543, 552, 553, 562, and 565 are similar to blisters of the same number of FIG. 15 of U.S. Pat. No. 8,895,295. Second-stage reaction zone 580 of FIG. 1 is similar to that of U.S. Pat. No. 8,895,295, but the second-stage wells 582 of high density array 581 are arranged in a somewhat different pattern. The more circular pattern of high density array 581 of FIG. 1 eliminates wells in corners and may result in more uniform filling of second-stage wells 582. As shown, the high density array 581 is provided with 102 second-stage wells 582. Pouch 510 is suitable for use in the FilmArray® instrument (BioFire Diagnostics, LLC, Salt Lake City, UT). However, it is understood that the pouch embodiment is illustrative only.

While other containers may be used, illustratively, pouch 510 may be formed of two layers of a flexible plastic film or other flexible material such as polyester, polyethylene terephthalate (PET), polycarbonate, polypropylene, polymethylmethacrylate, mixtures, combinations, and layers thereof that can be made by any process known in the art, including extrusion, plasma deposition, and lamination. For instance, each layer can be composed of one or more layers of material of a single type or more than one type that are laminated together. Metal foils or plastics with aluminum lamination also may be used. Other barrier materials are known in the art that can be sealed together to form the blisters and channels. If plastic film is used, the layers may be bonded together, illustratively by heat sealing. Illustratively, the material has low nucleic acid binding capacity.

For embodiments employing fluorescent monitoring, plastic films that are adequately low in absorbance and auto-fluorescence at the operative wavelengths can be used. Such material could be identified by testing different plastics, different plasticizers, and composite ratios, as well as different thicknesses of the film. For plastics with aluminum or other foil lamination, the portion of the pouch that is to be read by a fluorescence detection device can be left without the foil. For example, if fluorescence is monitored in second-stage wells 582 of the second-stage reaction zone 580 of pouch 510, then one or both layers at wells 582 would be left without the foil. In the example of PCR, film laminates composed of polyester (Mylar, DuPont, Wilmington DE) of about 0.0048 inch (0.1219 mm) thick and polypropylene films of 0.001-0.003 inch (0.025-0.076 mm) thick perform well. Illustratively, pouch 510 may be made of a clear material capable of transmitting approximately 80%-90% of incident light.

In the illustrative embodiment, the materials are moved between blisters by the application of pressure, illustratively pneumatic pressure, upon the blisters and channels. Accordingly, in embodiments employing pressure, the pouch material illustratively is flexible enough to allow the pressure to have the desired effect. The term "flexible" is herein used to describe a physical characteristic of the material of the pouch. The term "flexible" is herein defined as readily deformable by the levels of pressure used herein without cracking, breaking, crazing, or the like. For example, thin plastic sheets, such as Saran™ wrap and Ziploc® bags, as well as thin metal foil, such as aluminum foil, are flexible. However, only certain regions of the blisters and channels need be flexible, even in embodiments employing pneumatic pressure. Further, only one side of the blisters and channels need to be flexible, as long as the blisters and channels are readily deformable. Other regions of the pouch 510 may be made of a rigid material or may be reinforced with a rigid material. In other embodiments, flexible tubing may be used for portions of the sample container. Thus, it is understood that when the terms "flexible pouch" or "flexible sample container" or the like are used, only portions of the pouch or sample container need be flexible.

Illustratively, a plastic film may be used for pouch 510. A sheet of metal, illustratively aluminum, or other suitable material, may be milled or otherwise cut, to create a die having a pattern of raised surfaces. When fitted into a pneumatic press (illustratively A-5302-PDS, Janesville Tool Inc., Milton WI), illustratively regulated at an operating temperature of 195° C., the pneumatic press works like a printing press, melting the sealing surfaces of plastic film only where the die contacts the film. Likewise, the plastic film(s) used for pouch 510 may be cut and welded together using a laser cutting and welding device. Various components, such as PCR primers (illustratively spotted onto the film and dried), antigen binding substrates, magnetic beads, and zirconium silicate beads may be sealed inside various blisters as the pouch 510 is formed. Reagents for sample processing can be spotted onto the film prior to sealing, either collectively or separately. In one embodiment, nucleotide tri-phosphates (NTPs) are spotted onto the film separately from polymerase and primers, essentially eliminating activity of the polymerase until the reaction may be hydrated by an aqueous sample. If the aqueous sample has been heated prior to hydration, this creates the conditions for a true hot-start PCR and reduces or eliminates the need for expensive chemical hot-start components. In another embodiment, components may be provided in powder or pill form and are placed into blisters prior to final sealing.

Pouch 510 may be used in a manner similar to that described in U.S. Pat. No. 8,895,295. In one illustrative embodiment, a 300 µl mixture comprising the sample to be tested (100 µl) and lysis buffer (200 µl) may be injected into an injection port (not shown) in fitment 590 near entry channel 515a, and the sample mixture may be drawn into entry channel 515a. Water may also be injected into a second injection port (not shown) of the fitment 590 adjacent entry channel 515l, and is distributed via a channel (not shown) provided in fitment 590, thereby hydrating up to eleven different reagents, each of which were previously provided in dry form at entry channels 515b through 515l. Illustrative methods and devices for injecting sample and hydration fluid (e.g. water or buffer) are disclosed in U.S. Patent Application No. 2014-0283945, herein incorporated by reference in its entirety, although it is understood that these methods and devices are illustrative only and other ways of introducing sample and hydration fluid into pouch 510 are within the scope of this disclosure. These reagents illustratively may include freeze-dried PCR reagents, DNA extraction reagents, wash solutions, immunoassay reagents, or other chemical entities. Illustratively, the reagents are for nucleic acid extraction, first-stage multiplex PCR, dilution of the multiplex reaction, and preparation of second-stage PCR reagents, as well as control reactions. In the embodiment shown in FIG. 1, all that need be injected is the sample solution in one injection port and water in the other injection port. After injection, the two injection ports may be sealed.

For more information on various configurations of pouch 510 and fitment 590, see U.S. Pat. No. 8,895,295, already incorporated by reference.

After injection, the sample may be moved from injection channel 515a to lysis blister 522 via channel 514. Lysis blister 522 is provided with beads or particles 534, such as ceramic beads or other abrasive elements, and is configured for vortexing via impaction using rotating blades or paddles provided within the FilmArray® instrument. Bead-milling, by shaking, vortexing, sonicating, and similar treatment of the sample in the presence of lysing particles such as zirconium silicate (ZS) beads 534, is an effective method to form a lysate. It is understood that, as used herein, terms such as "lyse," "lysing," and "lysate" are not limited to rupturing cells, but that such terms include disruption of non-cellular particles, such as viruses.

Figure 2:
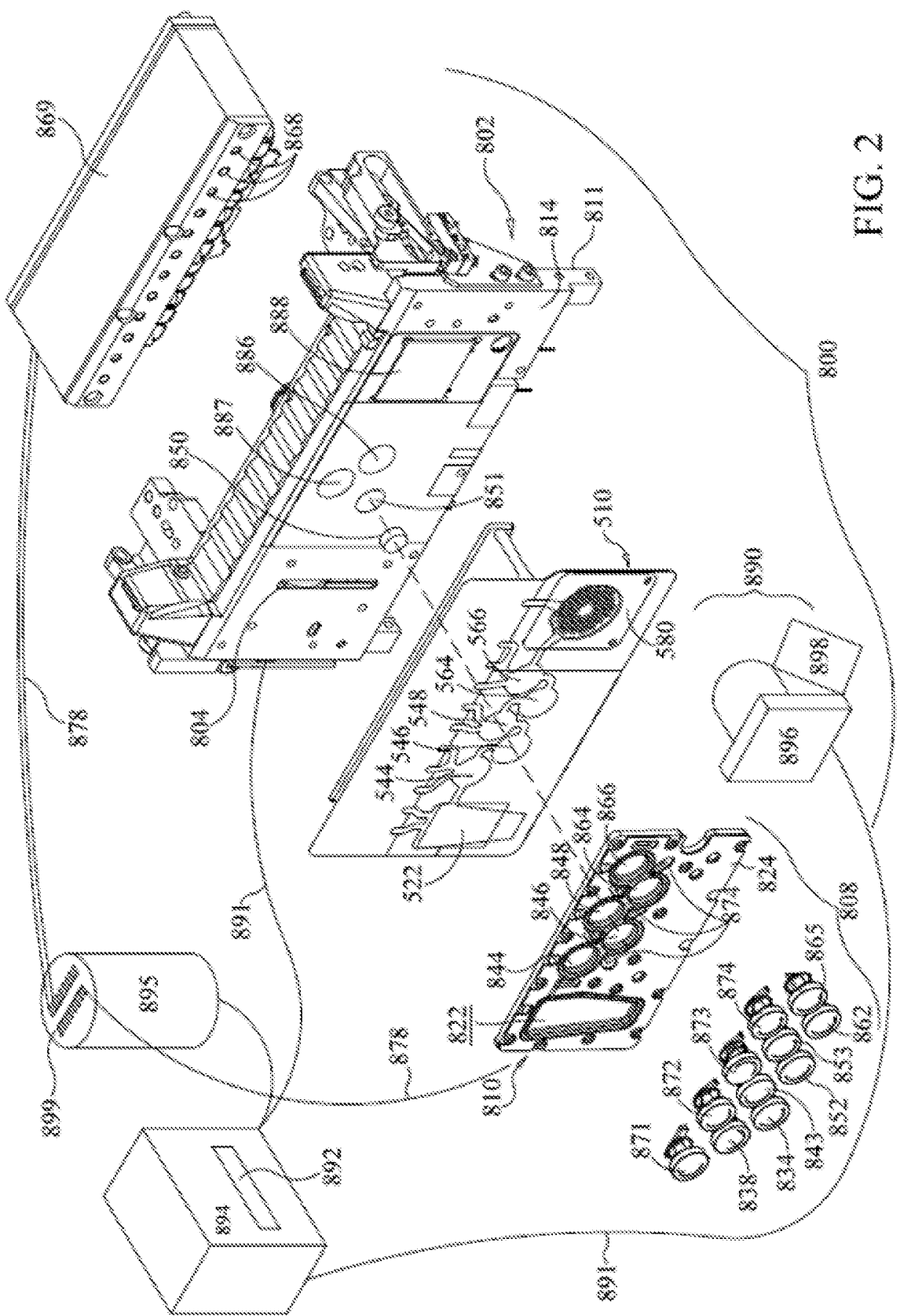
FIG. 2 is an exploded perspective view of an instrument for use with the pouch of FIG. 1, including the pouch of FIG. 1, according to an exemplary embodiment.
Figure 4:
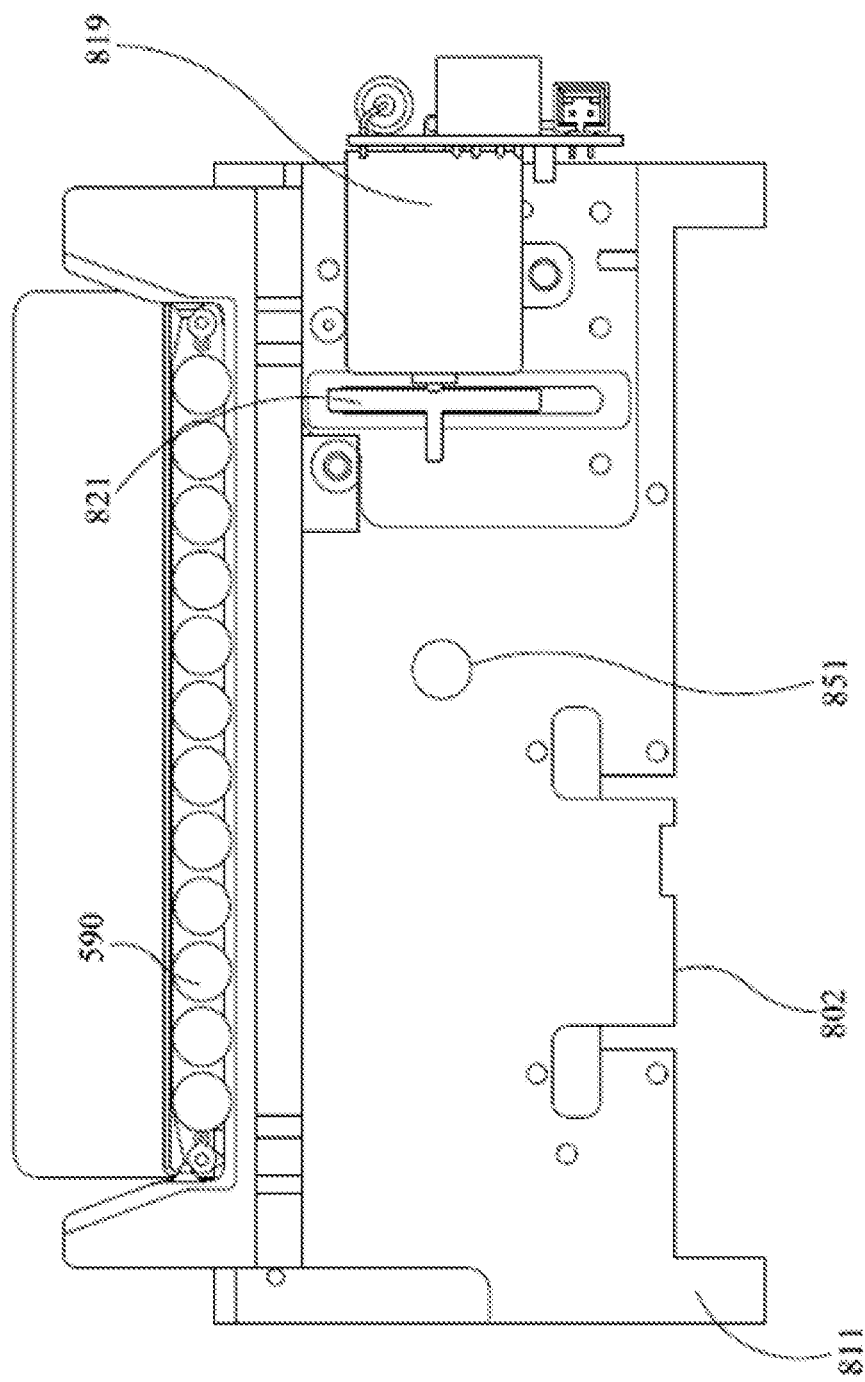
FIG. 4 shows a motor used in one illustrative embodiment of the instrument of FIG. 2.
Figure 5B:
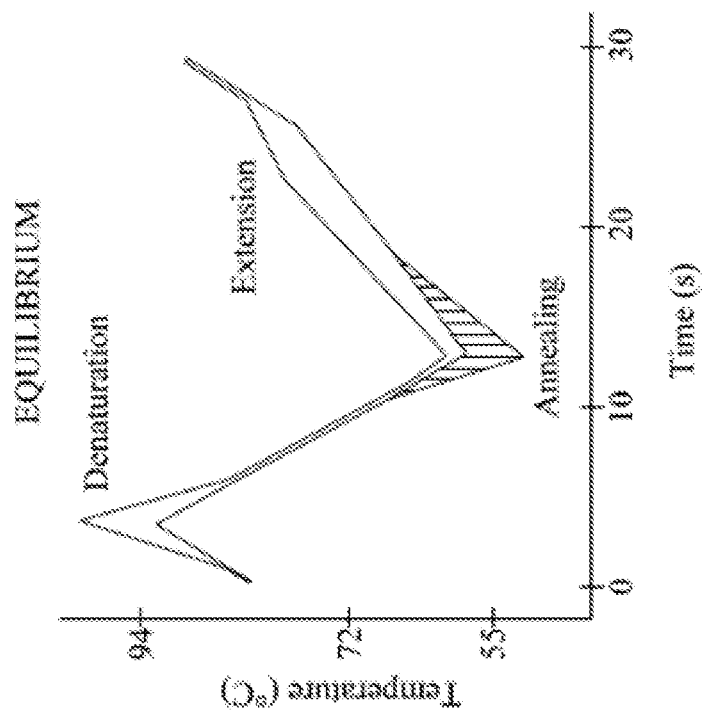
FIGS. 5A-5B show illustrative profiles for an equilibrium paradigm (FIG. 5a) and a kinetic paradigm (FIG. 5b) of PCR. Solid black represents denaturation, striped represents annealing, and solid white represents extension of the nucleic acids during thermal cycling.
Figure 5A:
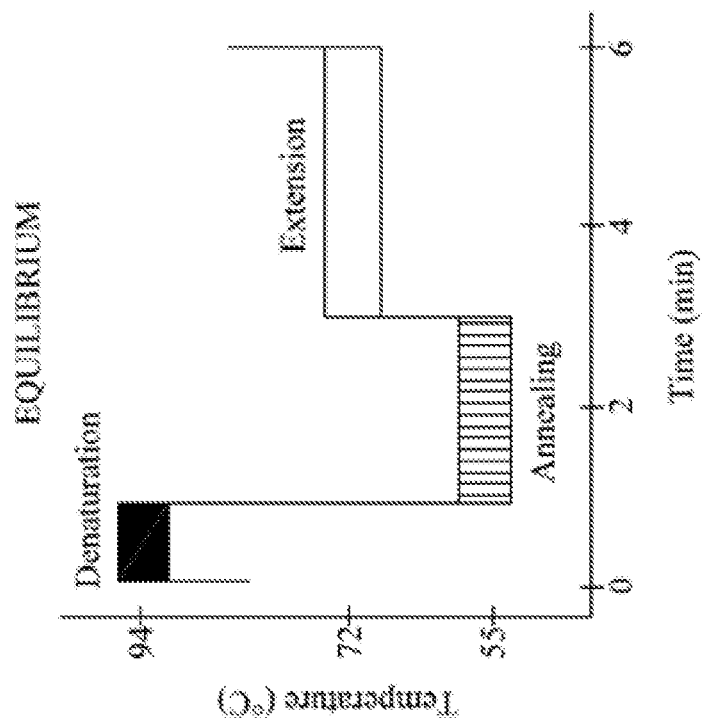

FIG. 4 shows a bead beating motor 819, comprising blades 821 that may be mounted on a first side 811 of support member 802, of instrument 800 shown in FIG. 2. Blades may extend through slot 804 to contact pouch 510. It is understood, however, that motor 819 may be mounted on other structures of instrument 800. In one illustrative embodiment, motor 819 is a Mabuchi RC-280SA-2865 DC Motor (Chiba, Japan), mounted on support member 802. In one illustrative embodiment, the motor is turned at 5,000 to 25,000 rpm, more illustratively 10,000 to 20,000 rpm, and still more illustratively approximately 15,000 to 18,000 rpm. For the Mabuchi motor, it has been found that 7.2V provides sufficient rpm for lysis. It is understood, however, that the actual speed may be somewhat slower when the blades 821 are impacting pouch 510. Other voltages and speeds may be used for lysis depending on the motor and paddles used. Optionally, controlled small volumes of air may be provided into the bladder 822 adjacent lysis blister 522. It has been found that in some embodiments, partially filling the adjacent bladder with one or more small volumes of air aids in positioning and supporting lysis blister during the lysis process. Alternatively, other structure, illustratively a rigid or compliant gasket or other retaining structure around lysis blister 522, can be used to restrain pouch 510 during lysis. It is also understood that motor 819 is illustrative only, and other devices may be used for milling, shaking, or vortexing the sample. In some embodiments, chemicals or heat may be used in addition to or instead of mechanical lysis.

Once the sample material has been adequately lysed, the sample is moved to a nucleic acid extraction zone, illustratively through channel 538, blister 544, and channel 543, to blister 546, where the sample is mixed with a nucleic acid-binding substance, such as silica-coated magnetic beads 533. Alternatively, magnetic beads 533 may be rehydrated, illustratively using fluid provided from one of the entry channel 515c-515e, and then moved through channel 543 to blister 544, and then through channel 538 to blister 522. The mixture is allowed to incubate for an appropriate length of time, illustratively approximately 10 seconds to approximately 10 minutes. In another embodiment, the magnetic beads may be present during bead beating, and incubation time may be reduced to 0 seconds. A retractable magnet located within the instrument adjacent blister 546 captures the magnetic beads 533 from the solution, forming a pellet against the interior surface of blister 546. If incubation takes place in blister 522, multiple portions of the solution may need to be moved to blister 546 for capture. The liquid is then moved out of blister 546 and back through blister 544 and into blister 522, which is now used as a waste receptacle. One or more wash buffers from one or more injection channels 515c to 515e are provided via blister 544 and channel 543 to blister 546. Optionally, the magnet is retracted and the magnetic beads 533 are washed by moving the beads back and forth from blisters 544 and 546 via channel 543. Once the magnetic beads 533 are washed, the magnetic beads 533 are recaptured in blister 546 by activation of the magnet, and the wash solution is then moved to blister 522. This process may be repeated as necessary to wash the lysis buffer and sample debris from the nucleic acid-binding magnetic beads 533.

After washing, elution buffer stored at injection channel 515f is moved to blister 548, and the magnet is retracted. The solution is cycled between blisters 546 and 548 via channel 552, breaking up the pellet of magnetic beads 533 in blister 546 and allowing the captured nucleic acids to dissociate from the beads and come into solution. The magnet is once again activated, capturing the magnetic beads 533 in blister 546, and the eluted nucleic acid solution is moved into blister 548.

In some embodiments, it may be desirable to preheat the instrument prior to PCR. Preheating of the heaters for either or both of the amplification zones (e.g., locations of the first-stage amplification and second second-stage amplification) may take place prior to placing pouch 510 into instrument 800, or heating may take place contemporaneously with any of the above steps. Preheating of the amplification zones may decrease the time needed for the first few amplification cycles and may also provide for a more uniformly heated amplification zone. Also, preheating of blister 546 may be desirable in embodiments using heated lysis.

First-stage PCR master mix from injection channel 515g is mixed with the nucleic acid sample in blister 548. Optionally, the mixture is mixed by forcing the mixture between 548 and 564 via channel 553. Also optionally, the first-stage PCR master mix may be preheated, illustratively during the preheating of the amplification zones. Illustratively, the first-stage PCR master mix may be heated to a temperature that is above the annealing temperature for the PCR reaction. After several cycles of mixing, the solution is contained in blister 564, where a pellet of first-stage PCR primers is provided, at least one set of primers for each target, and first-stage multiplex PCR is performed using heater 886. If RNA targets are present, an RT step may be performed prior to or simultaneously with the first-stage multiplex PCR. First-stage multiplex PCR temperature cycling in the FilmArray® instrument is illustratively performed for 15-20 cycles, although other levels of amplification may be desirable, depending on the requirements of the specific application. The first-stage PCR master mix may be any of various master mixes, as are known in the art. In one illustrative example, the first-stage PCR master mix may be any of the chemistries disclosed in U.S. Pat. No. 9,932,634, herein incorporated by reference, for use with PCR protocols taking 20 seconds or less per cycle.

It is understood that a heater 887 may also be provided for heating the sample in blister 548, where first-stage multiplex PCR occurs in a larger volume, using both blisters 548 and 564. Heaters 886 and 887 may be thermocycled together, allowing for a larger volume to be thermocycled at once, or heaters 886 and 887 may be provided at two different temperatures, allowing for thermocycling by repeatedly moving the mixture between blisters 548 and 564. Alternatively, heaters 886 and 887 may be replaced by a single larger heater that simultaneously thermocycles the contents of both blisters 548 and 565.

Illustrative methods of speeding up first-stage amplification using this embodiment are described in Example 2, wherein the volume of the PCR mixture is reduced after at least one cycle, with optional further volume reductions. In one illustrative embodiment, volume may be reduced by closing seal 853, opening seal 852, and then compressing the various bladders to move some or all of the liquid from blister 548, illustratively to blister 522. Subsequently, seal 852 may be closed, seal 853 opened, and the volume may be redistributed between blisters 548 and 564. This may be repeated multiple times. In one illustrative embodiment, once the volume is reduced sufficiently, PCR may continue using only one of blisters 548 or 564, with using its respective heater 886 or 887, thereby reducing the thermal mass of the heaters and saving energy by only using one heater for this amplification. Other ways of reducing the volume of the sample and reducing the thermal mass of the heaters, thereby reducing energy consumption, are contemplated. However, it is understood that such methods are applicable to other embodiments, including embodiments where first-stage amplification occurs only in blister 564 or embodiments where heaters 886 and 887 are kept at different temperatures and thermocycling occurs by moving the sample repeatedly between blisters 548 and 564. Such methods are also applicable to other pouch-based and non-pouch-based systems. In non-pouch-based systems, volume may be reduced by pipetting or suctioning PCR mixture from the sample well, or by other methods, as are known in the art.

After first-stage PCR has proceeded for the desired number of cycles, the sample may be diluted, illustratively by forcing most of the sample back into blister 548, leaving only a small amount in blister 564, and adding second-stage PCR master mix from injection channel 515*i*. Alternatively, a dilution buffer from 515*i* may be moved to blister 566 then mixed with the amplified sample in blister 564 by moving the fluids back and forth between blisters 564 and 566. If desired, dilution may be repeated several times or as many times as desired, using dilution buffer from injection channels 515*j* and 515*k*, or injection channel 515*k* may be reserved, illustratively, for sequencing or for other post-PCR analysis, and then adding second-stage PCR master mix from injection channel 515*h* to some or all of the diluted amplified sample. It is understood that the level of dilution may be adjusted by altering the number of dilution steps or by altering the percentage of the sample discarded prior to mixing with the dilution buffer or second-stage PCR master mix comprising components for amplification, illustratively a polymerase, dNTPs, and a suitable buffer, although other components may be suitable, particularly for non-PCR amplification methods. If desired, this mixture of the sample and second-stage PCR master mix may be pre-heated in one or both of blisters 548 and 564 prior to movement to second-stage wells 582 for second-stage amplification. Illustratively, the second-stage PCR master mix may be heated to a temperature that is above the annealing temperature for the PCR reaction. Such preheating may obviate the need for a hot-start component (antibody, chemical, or otherwise) in the second-stage PCR mixture. Similar preheating may be used to obviate the need for a hot-start component in first-stage PCR.

The illustrative second-stage PCR master mix is incomplete, lacking primer pairs, and each of the 102 second-stage wells 582 is pre-loaded with a specific PCR primer pair. If desired, second-stage PCR master mix may lack other reaction components, and these components may be pre-loaded in the second-stage wells 582 as well. Each primer pair may be similar to or identical to a first-stage PCR primer pair or may be nested within the first-stage primer pair.

Movement of the sample from blister 564 to the second-stage wells 582 completes the PCR reaction mixture. Once high density array 581 is filled, the individual second-stage reactions are sealed in their respective second-stage blisters by any number of means, as is known in the art. Illustrative ways of filling and sealing the high density array 581 without cross-contamination are discussed in U.S. Pat. No. 8,895,295, already incorporated by reference. Illustratively, the various reactions in wells 582 of high density array 581 are simultaneously or individually thermal cycled, illustratively with one or more Peltier devices, although other means for thermal cycling are known in the art and can be used.

In certain embodiments, second-stage PCR master mix contains the dsDNA binding dye LCGreen® Plus (BioFire Diagnostics, LLC) to generate a signal indicative of amplification. However, it is understood that this dye is illustrative only, and that other signals may be used, including other dsDNA binding dyes and probes that are labeled fluorescently, radioactively, chemiluminescently, enzymatically, or the like, as are known in the art. Alternatively, second-stage wells 582 of array 581 may be provided without a signal, with results reported through subsequent processing.

Figure 3:
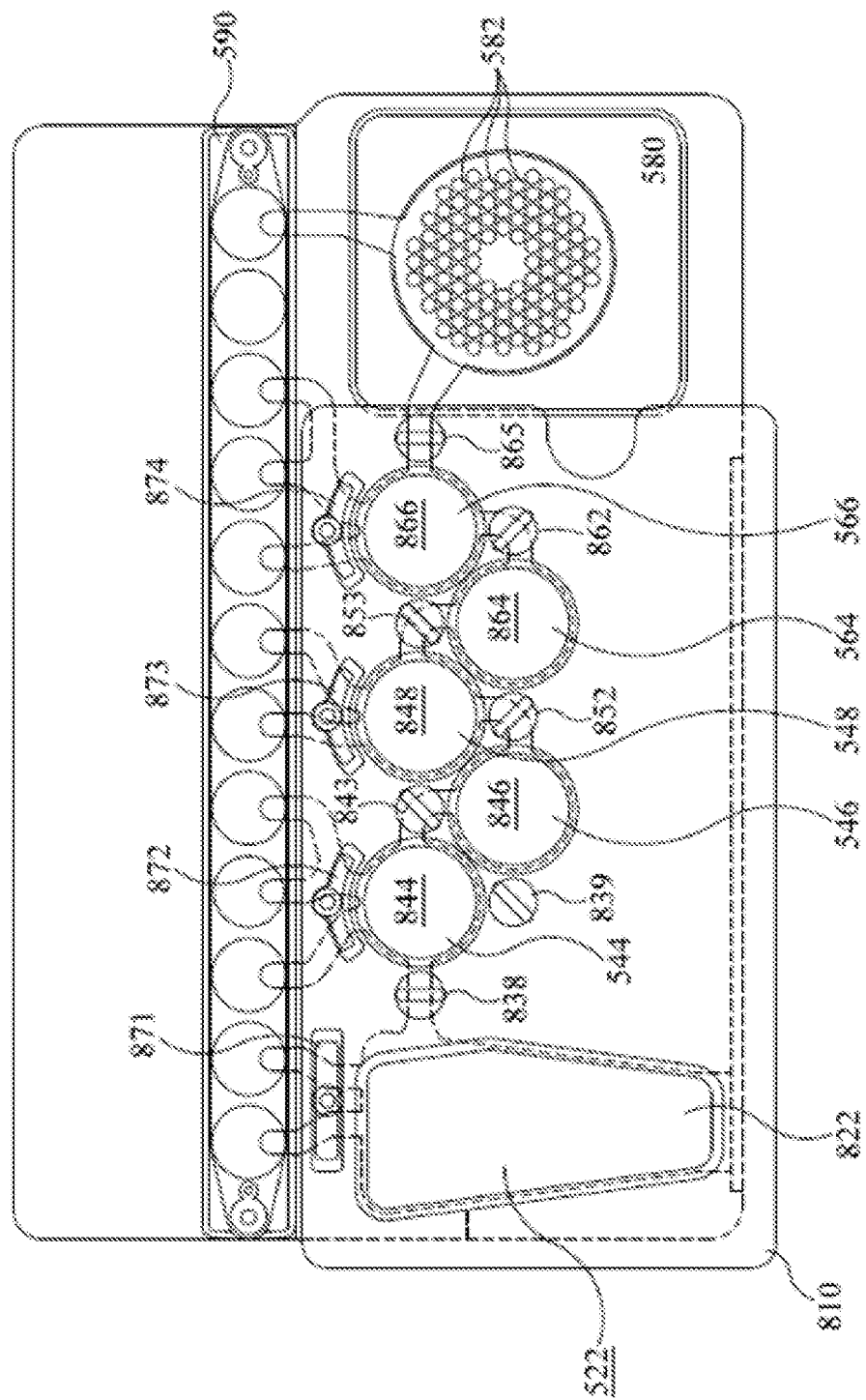
FIG. 3 shows a partial cross-sectional view of the instrument of FIG. 2, including the bladder components of FIG. 2, with the pouch of FIG. 1 shown in dashed lines.

When pneumatic pressure is used to move materials within pouch 510, in one embodiment, a "bladder" may be employed. The bladder assembly 810, a portion of which is shown in FIGS. 2-3, includes a bladder plate 824 housing a plurality of inflatable bladders 822, 844, 846, 848, 864, and 866, each of which may be individually inflatable, illustratively by a compressed gas source. Because the bladder assembly 810 may be subjected to compressed gas and used multiple times, the bladder assembly 810 may be made from tougher or thicker material than the pouch. Alternatively, bladders 822, 844, 846, 848, 864, and 866 may be formed from a series of plates fastened together with gaskets, seals, valves, and pistons. Other arrangements are within the scope of present disclosure. Alternatively, an array or mechanical actuators and seals may be used to seal channels and direct movement of fluids between blisters. A system of mechanical seals and actuators that may be adapted for the instruments described herein is described in detail in PCT/US2017/044333, the entirety of which is incorporated herein by reference.

Success of the secondary PCR reactions is dependent upon template generated by the multiplex first-stage reaction. Typically, PCR is performed using DNA of high purity. Methods such as phenol extraction or commercial DNA extraction kits provide DNA of high purity. Samples processed through the pouch 510 may require accommodations be made to compensate for a less pure preparation. PCR may be inhibited by components of biological samples, which is a potential obstacle. Illustratively, hot-start PCR, higher concentration of Taq polymerase enzyme, adjustments in $MgCl_2$ concentration, adjustments in primer concentration, and addition of adjuvants (such as DMSO, TMSO, or glycerol) optionally may be used to compensate for lower nucleic acid purity. While purity issues are likely to be more of a concern with first-stage amplification, it is understood that similar adjustments may be provided in the second-stage amplification as well.

When pouch 510 is placed within the instrument 800, the bladder assembly 810 is pressed against one face of the pouch 510, so that if a particular bladder is inflated, the pressure will force the liquid out of the corresponding blister in the pouch 510. In addition to bladders corresponding to many of the blisters of pouch 510, the bladder assembly 810 may have additional pneumatic actuators, such as bladders or pneumatically-driven pistons, corresponding to various channels of pouch 510. FIGS. 2-3 show an illustrative plurality of pistons or hard seals 838, 843, 852, 853, and 865 that correspond to channels 538, 543, 553, and 565 of pouch 510, as well as seals 871, 872, 873, 874 that minimize backflow into fitment 590. When activated, hard seals 838, 843, 852, 853, and 865 form pinch valves to pinch off and close the corresponding channels. To confine liquid within a particular blister of pouch 510, the hard seals are activated over the channels leading to and from the blister, such that the actuators function as pinch valves to pinch the channels shut. Illustratively, to mix two volumes of liquid in different blisters, the pinch valve actuator sealing the connecting channel is activated, and the pneumatic bladders over the blisters are alternately pressurized, forcing the liquid back and forth through the channel connecting the blisters to mix the liquid therein. The pinch valve actuators may be of various shapes and sizes and may be configured to pinch off more than one channel at a time. While pneumatic actuators are discussed herein, it is understood that other ways of providing pressure to the pouch are contemplated, including various electromechanical actuators such as linear stepper motors, motor-driven cams, rigid paddles driven by pneumatic, hydraulic or electromagnetic forces, rollers, rocker-arms, and in some cases, cocked springs. Such actuators may be positioned to provide enough pressure to force all or most of the fluid from its respective blister, or actuators may be moved only partially in the direction of the blister to force a portion of the fluid from its respective blister. In addition, there are a variety of methods of reversibly or irreversibly closing channels in addition to applying pressure normal to the axis of the channel. These include kinking the bag across the channel, heat-sealing, rolling an actuator, and a variety of physical valves sealed into the channel such as butterfly valves and ball valves. Additionally, small Peltier devices or other temperature regulators may be placed adjacent the channels and set at a temperature sufficient to freeze the fluid, effectively forming a seal. Also, while the design of FIG. 1 is adapted for an automated instrument featuring actuator elements positioned over each of the blisters and channels, it is also contemplated that the actuators could remain stationary, and the pouch 510 could be transitioned such that a small number of actuators could be used for several of the processing stations including sample disruption, nucleic-acid capture, first and second-stage PCR, and processing stations for other applications of the pouch 510 such as immuno-assay and immuno-PCR. Rollers acting on channels and blisters could prove particularly useful in a configuration in which the pouch 510 is translated between stations. Thus, while pneumatic actuators are used in the presently disclosed embodiments, when the term "pneumatic actuator" is used herein, it is understood that other actuators and other ways of providing pressure may be used, depending on the configuration of the pouch and the instrument.

Turning back to FIG. 2, each pneumatic actuator is connected to compressed air source 895 via valves 899. While only several hoses 878 are shown in FIG. 2, it is understood that each pneumatic fitting is connected via a hose 878 to the compressed gas source 895. Compressed gas source 895 may be a compressor, or, alternatively, compressed gas source 895 may be a compressed gas cylinder, such as a carbon dioxide cylinder. Compressed gas cylinders are particularly useful if portability is desired. Other sources of compressed gas are within the scope of the present disclosure. Similar pneumatic controls may be provided in the embodiments of FIGS. 12-14, for control of fluids in pouch 1400, or other actuators, servos, or the like may be provided.

Several other components of instrument 810 are also connected to compressed gas source 895. A magnet 850, which is mounted on a second side 814 of support member 802, is illustratively deployed and retracted using gas from compressed gas source 895 via hose 878, although other methods of moving magnet 850 are known in the art and can be used. Magnet 850 sits in recess 851 in support member 802. It is understood that recess 851 can be a passageway through support member 802, so that magnet 850 can contact blister 546 of pouch 510. However, depending on the material of support member 802, it is understood that recess 851 need not extend all the way through support member 802, as long as when magnet 850 is deployed, magnet 850 is close enough to provide a sufficient magnetic field at blister 546, and when magnet 850 is fully retracted, magnet 850 does not significantly affect any magnetic beads 533 present in blister 546. While reference is made to retracting magnet 850, it is understood that an electromagnet may be used and the electromagnet may be activated and inactivated by controlling flow of electricity through the electromagnet. Thus, while this specification discusses withdrawing or retracting the magnet, it is understood that these terms are broad enough to incorporate other ways of withdrawing the magnetic field. It is understood that the pneumatic connections may be pneumatic hoses or pneumatic air manifolds, thus reducing the number of hoses or valves required. It is understood that similar magnets and methods for activating the magnets may be used in the embodiments of FIGS. 12-14.

The various pneumatic pistons 868 of pneumatic piston array 869 are also connected to compressed gas source 895 via hoses 878. While only two hoses 878 are shown connecting pneumatic pistons 868 to compressed gas source 895, it is understood that each of the pneumatic pistons 868 are connected to compressed gas source 895. Twelve pneumatic pistons 868 are shown in FIG. 12 as an example of one configuration that may be used.

A pair of temperature control elements are mounted on a second side 814 of support 802. As used herein, the term "temperature control element" refers to a device that adds heat to or removes heat from a sample. Illustrative examples of a temperature control element include, but are not limited to, heaters, coolers, Peltier devices, resistance heaters, induction heaters, electromagnetic heaters, thin film heaters, printed element heaters, positive temperature coefficient heaters, and combinations thereof. A temperature control element may include multiple heaters, coolers, Peltiers, etc. In one aspect, a given temperature control element may include more than one type of heater or cooler. For instance, an illustrative example of a temperature control element may include a Peltier device with a separate resistive heater applied to the top and/or the bottom face of the Peltier. While the term "heater" is used throughout the specification, it is understood that other temperature control elements may be used to adjust the temperature of the sample.

As discussed above, first-stage heater 886 may be positioned to heat and cool the contents of blister 564 for first-stage PCR. As seen in FIG. 2, second-stage heater 888 may be positioned to heat and/or cool the contents of second-stage blisters 582 of array 581 of pouch 510, for second-stage PCR. It is understood, however, that these heaters could also be used for other heating or cooling purposes, and that other heaters may be included, as appropriate for the particular application.

When fluorescent detection is desired, an optical array 890 may be provided. As shown in FIG. 2, optical array 890 includes a light source 898, illustratively a filtered LED light source, filtered white light, or laser illumination, and a camera 896. Camera 896 illustratively has a plurality of photodetectors each corresponding to a second-stage well 582 in pouch 510. Alternatively, camera 896 may take images that contain all of the second-stage wells 582, and the image may be divided into separate fields corresponding to each of the second-stage wells 582. Depending on the configuration, optical array 890 may be stationary, or optical array 890 may be placed on movers attached to one or more motors and moved to obtain signals from each individual second-stage well 582. It is understood that other arrangements are possible. Such orientation is illustrative only and may be determined by spatial constraints within the instrument. Provided that second-stage reaction zone 580 is provided in an optically transparent material, photodetectors and heaters may be located on either side of array 581.

As shown, a computer 894 controls valves 899 of compressed air source 895, and thus controls all of the pneumatics of instrument 800. In addition, many of the pneumatic systems in the instrument may be replaced with mechanical actuators, pressure applying means, and the like in other embodiments. Computer 894 also controls heaters 886, 887, and 888, and optical array 890. Each of these components is connected electrically, illustratively via cables 891, although other physical or wireless connections are within the scope of this invention. It is understood that computer 894 may be housed within instrument 800 or may be external to instrument 800. Further, computer 894 may include built-in circuit boards that control some or all of the components, and may also include an external computer, such as a desktop or laptop PC or a smartphone, to receive and display data from the optical array. An interface, illustratively a keyboard interface, may be provided including keys for inputting information and variables such as temperatures, cycle times, etc. Illustratively, a display 892 is also provided. Display 892 may be an LED, LCD, or other such display, for example.

Other instruments teach PCR within a sealed flexible container. See, e.g., U.S. Pat. Nos. 6,645,758 and 6,780,617, and 9,586,208, herein incorporated by reference. However, including the cell lysis within the sealed PCR vessel can improve ease of use and safety, particularly if the sample to be tested may contain a biohazard. In the embodiments illustrated herein, the waste from cell lysis, as well as that from all other steps, remains within the sealed pouch. Still, it is understood that the pouch contents could be removed for further testing.

FIG. 2 shows an illustrative instrument 800 that could be used with pouch 510. Instrument 800 includes a support member 802 that could form a wall of a casing or be mounted within a casing. Instrument 800 may also include a second support member (not shown) that is optionally movable with respect to support member 802, to allow insertion and withdrawal of pouch 510. Illustratively, a lid may cover pouch 510 once pouch 510 has been inserted into instrument 800. In another embodiment, both support members may be fixed, with pouch 510 inserted between the supports and held into place by other mechanical means or by pneumatic pressure.

In the illustrative example, heaters 886, 887, and 888 are mounted on support member 802. However, it is understood that this arrangement is illustrative only and that other arrangements are possible. Illustrative heaters include Peltiers and other block heaters, resistance heaters, electromagnetic heaters, and thin film heaters, as are known in the art, to thermocycle the contents of blister 864 and second-stage reaction zone 580. Bladder plate 810, with bladders 822, 844, 846, 848, 864, 866, hard seals 838, 843, 852, 853, and seals 871, 872, 873, 874 form bladder assembly 808, which may illustratively be mounted on a moveable support structure that may be moved toward pouch 510, such that the pneumatic actuators are placed in contact with pouch 510. When pouch 510 is inserted into instrument 800 and the movable support member is moved toward support member 802, the various blisters of pouch 510 are in a position adjacent to the various bladders of bladder assembly 810 and the various seals of assembly 808, such that activation of the pneumatic actuators may force liquid from one or more of the blisters of pouch 510 or may form pinch valves with one or more channels of pouch 510. The relationship between the blisters and channels of pouch 510 and the bladders and seals of assembly 808 is illustrated in more detail in FIG. 3.

Figure 6:
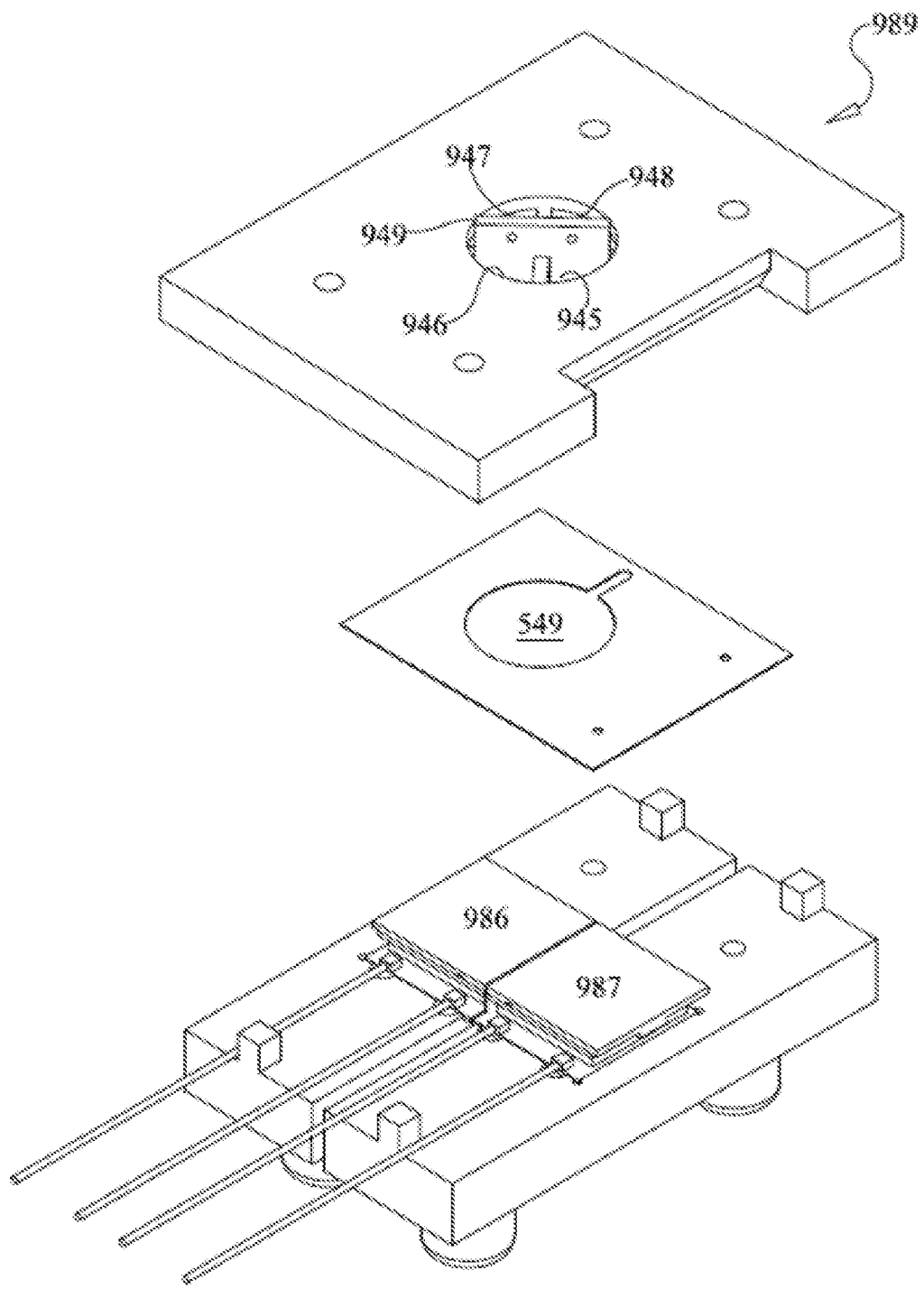
FIG. 6 is an exploded view of an alternative heating embodiment for first-stage PCR for the instrument of FIG. 2.
Figure 7:
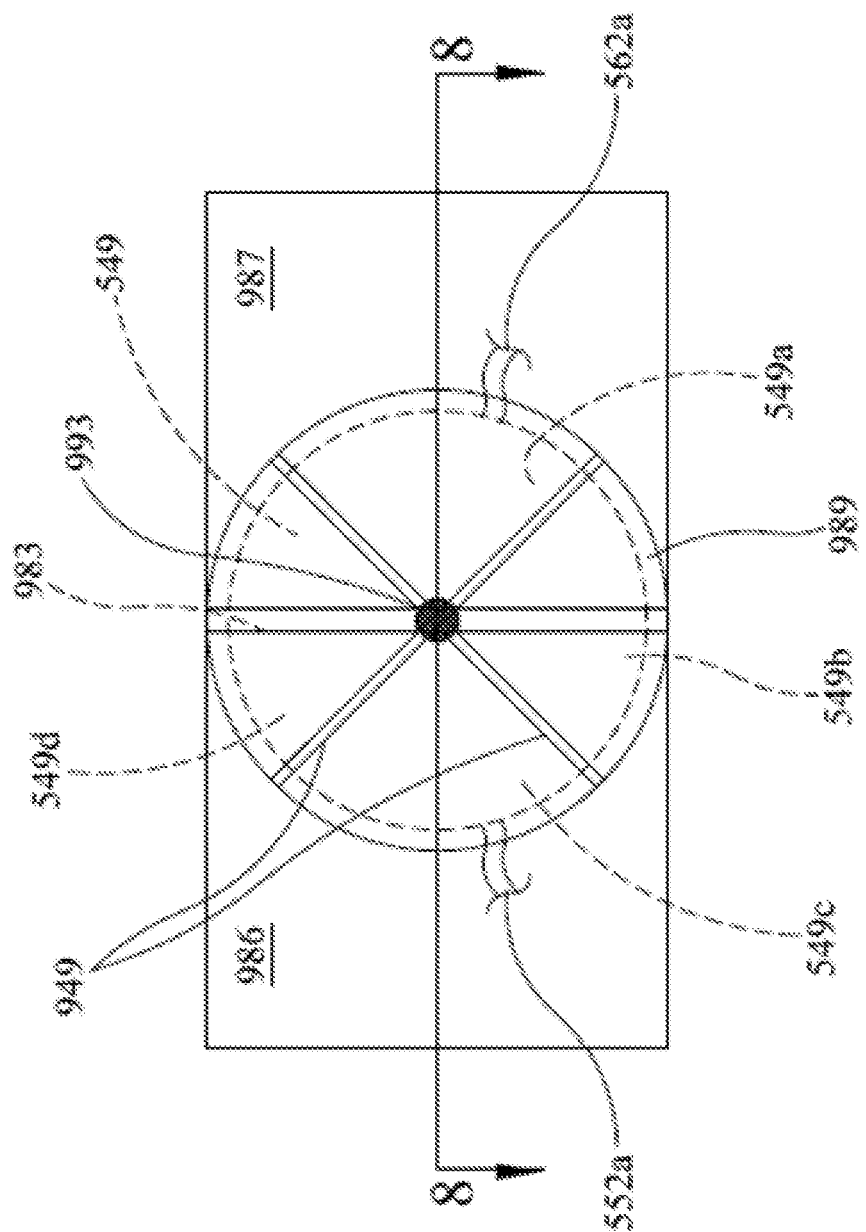
FIG. 7 is a top view of the heating format of FIG. 6.

By thermocycling heaters 886, 888, the run time for the PCR portions necessarily needs to be at least as long as the heater takes to get to a suitable temperature at each transition. It is understood that the run time could be reduced if the temperature of the heaters does not need to be changed. FIGS. 6-8 show another embodiment for the first-stage PCR amplification. In this illustrative embodiment, blisters 548 and 564 may be replaced with a single blister 549, and the illustrative instrument may be provided with a temperature control element that includes heaters 986 and 987. However, it is understood that one of blisters 548 or 564 may be used and smaller heaters 986, 987 may be used, or that blister 549 may be used by itself in combination with other embodiments that may or may not include components for cell lysis and/or additional amplification. Heaters 986, 987 may be Peltier devices, resistance heaters, induction heaters, electromagnetic heaters, thin film heaters, printed element heaters, positive temperature coefficient heaters, other heaters as are known in the art, or combinations of heater types (e.g., a heater element that includes a Peltier thermoelectric heater/cooler device and a resistive heater). However, unlike heater 886 that is provided to thermocycle between an annealing and a denaturation temperature, in one example, heater 986 may be provided at a suitable denaturation temperature, illustratively 94° C., and heater 987 may be provided at a suitable annealing temperature, illustratively 60° C., although other illustrative denaturation and annealing temperatures may be used, as are known in the art. In some embodiments, it may be desirable to set heater 986 higher than 94° C. and set heater 987 at a temperature lower than 60° C., as fluid may be circulated through control of each of these heaters quickly as the fluid reaches temperature, thereby increasing ramp rate. Such embodiments may be suited for use with enhanced primer and polymerase concentrations. Illustratively, an insulating spacer 983 may be provided between heater 986 and heater 987. Any suitable insulating material may be used, including foam, plastic, rubber, air, vacuum, glass, or any other suitable material illustratively of low conductivity. In embodiments where heaters 986 and 987 are held at a generally constant temperature, run time and energy usage may be substantially reduced.

In the illustrative example, a wiper head 910 comprising a wiper 989 engages top surface 549b of blister 549. When fluid is moved into blister 549, wiper 989 is moved so that body 913 of wiper 989 forces blister 549 into contact with heaters 986, 987, so that a portion of blister 549 is in contact with each of the heaters, to permit thermal transfer from each of the heaters to a portion of blister 549. One or more blades 949 may then be used to move the sample 572 from one area of blister 549 to another area of blister 549.

Figure 8A:
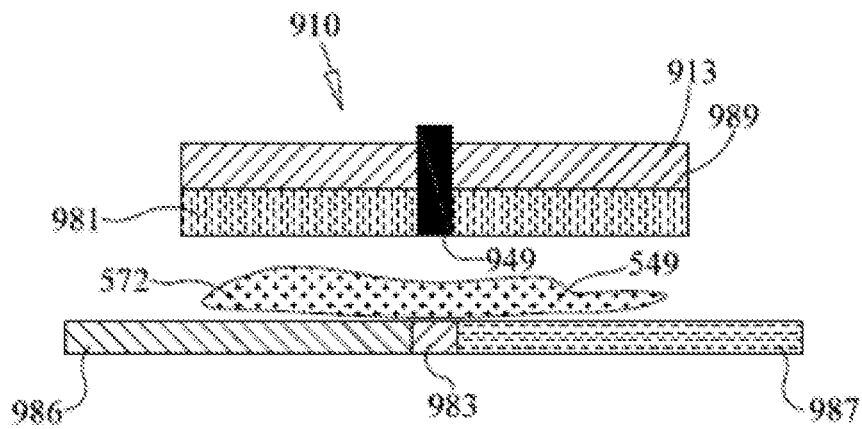
FIGS. 8A-8D show a cross-sectional view of FIG. 7 and also illustrate how a wiper may contact a fluid-filled blister, according to one embodiment of the present disclosure.
Figure 8B:
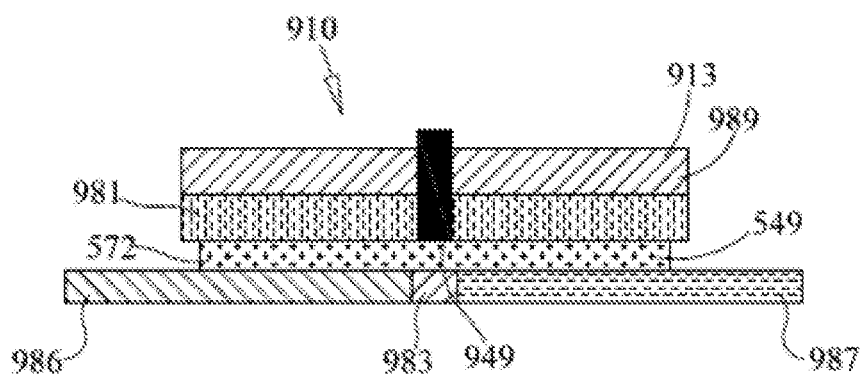

Often when a fluid enters a compartment, the fluid may remain near the entry to that compartment or the contents of a compartment may not be fully mixed. This is schematically illustrated in FIG. 8A where the illustrated blister 549 has adopted an irregular shape and may not be in good contact with the heaters 986 and 987. Depending on the volume of the blister 549, the volume of sample 572 added, the contents of the sample, etc., the fluid 572 may be irregularly shaped with the bulk of the fluid collected near where the sample is injected into the blister. This may be particularly true where the compartment is expandable and is partially or fully collapsed prior to the addition of the fluid, or in other situations when the fluid may be less than sufficient to fill the compartment completely. One can imagine an embodiment wherein sample 572 enters blister 549 through channel 552a and remains near channel 552a so that engagement of blade 949 traps most or all of sample 572 in section 549c. Accordingly, it may be desirable to spread the fluid across the compartment prior to engagement of a blade. Thus, as illustrated in FIG. 8B, wiper head 910 may be lowered until it contacts the blister 549 to spread sample 572 across blister 549 to evenly distribute the fluid 572 in the blister 549, to cause the blister 549 to adopt a regular shape, and to press the blister 549 into good, consistent contact with the heaters 986 and 987.

In one embodiment, the wiper head 910 may be provided with a pressure member (or members) 981 that places pressure on blister 549 and spreads sample 572 across blister 549. Illustratively, use of member 981 has several benefits. One is that more of sample 572 may be spread across heaters 986, 987 in a thinner layer, thus increasing the surface area to volume ratio, which should improve heat transfer to and from sample 572. Likewise, since the fluid is being rapidly thermocycled—i.e., the liquid of sample 572 is rapidly being raised and lowered in temperature by heaters 986 and 987, spreading the liquid into a thin layer in blister 549 may decrease the dwell time at any given temperature and allow more of the sample to hit the target temperature more quickly. Also, depending on the shape of wiper 989, as discussed below, pressure from member 981 onto blister 549 spreads sample 572 so that engagement of blade 949 of wiper 989 divides the sample 572 in blister 549 into relatively even or proportional volumes. Pressure from member 981 prior to engagement of blade 949 would force some of sample 572 into each of the sections of blister 549.

In one embodiment, member 981 is compressible or semi-compressible (e.g., formed of or comprising a compressible or semi-compressible material). Such materials include compressible or semi-compressible foams, plastics, or rubbers, or may be a more solid material but have a spring-loaded, elastomeric, or other biasing member or force between member 981 and wiper body 913, such that when sample 572 is moved into blister 549, sample 572 is spread across blister 549 but member 981 compresses appropriately to permit sufficient space for sample 572. Other compressible or semi-compressible materials may be used as are known in the art. Alternatively, member 981 may be substantially rigid and set to a position such as to provide only a sufficient space between member 981 and heaters 986, 987 to force the sample 572 to spread across blister 549.

Figure 8C:
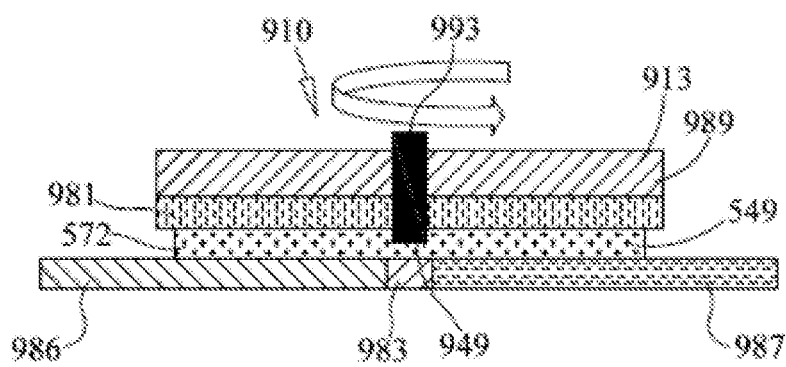
Figure 8D:
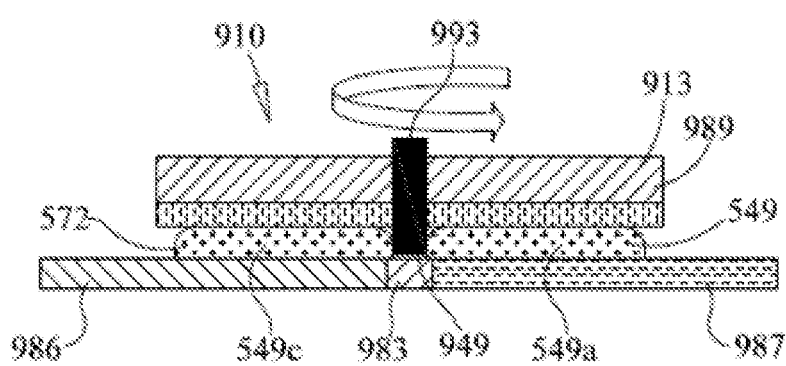

In the illustrative embodiment, wiper 989 has an x-shaped blade 949 that extends through member 981 and divides wiper 989 into four sections 945, 946, 947, 948, as illustrated in FIG. 6. As illustrated in FIGS. 8C and 8D, the wiper 989 and the blade 949 may contact the blister in at least two modes. As illustrated in FIG. 8C, the wiper 989 may be lowered until member 981 is compressed partially and the blade 949 impinges partially on the blister 549. If the wiper head 910 is rotated in the mode of FIG. 8C, the action of blade 949 can be used to provide a stirring action to thoroughly mix the contents 572 of the blister 549.

If the wiper head is lowered further, as illustrated in FIG. 8D, such that member 981 is further compressed and the blade 949 fully impinges in the blister 549, then the blade may divide the blister into discrete sections. For example, with an x-shaped blade 949, as illustrated in FIG. 7, the blade 949 may contact blister 549 with enough pressure such that blade 949 divides blister 549 into corresponding four sections, 549a, 549b, 549c, and 549d. Rotation of wiper 989 around axis 993 forces fluid within blister 549 into a circular motion around blister 549. In one embodiment, blade 949 allows portions of the fluid to be heated by each of the heaters 986 and 987 simultaneously, and moves portions of fluid from temperature control of one heater while permitting other portions of fluid to be under control of the other heater. Member 981 compresses the contents of blister 549. Thus, in addition to spreading out the fluid 572 in the blister 549 and improving contact between the blister 549 and the heaters 986 and 987, member 981 may also plunge the contents of blister 549 to another blister. For example, after first-stage thermal cycling is complete, an exit channel may be opened, which opens a path for fluid to flow out of the blister as member 981 returns to its original shape. In one embodiment, fluid may only flow out of the quadrant of the blister that is fluidly connected with the channel. Wiper 989 may be rotated so that each quadrant is connected with the exit channel in turn.

Illustratively, blade 949 may be a rubber or elastomeric material, or a non-stick material such as Teflon or Delrin having enough stiffness to divide blister 549 into sections and to move fluid within blister 549, but not puncture or tear blister 549, although it is understood that such materials are illustrative only and that other materials may be used, as are known in the art. Blade 949 alternatively may be replaced by rollers or other configurations to force movement of fluid within blister 549. Wiper head 910, including wiper 989 and blade 949, may be moved into position and rotated by any motor, cam, crank, gear mechanism, hydraulics, pneumatics, or other means, as are known in the art. Such movement may be continuous or wiper 989 and blade 949 may be moved step-wise with pauses, illustratively 0.1 seconds to a minute or more, thus holding portions of the sample in control of each of the heaters 986, 987 before being moved to its next position and holding different portions of the sample in control of each of the heaters 986, 987. The motion of wiper 989 may be circular, in a clockwise or counter-clockwise motion, or may reverse directions, alternating between clockwise and counter-clockwise. It is understood that wiper body 913 and blade 949 may be a single fixed unit and move as a single fixed unit, or body 913 may be moved into and out of contact with blister 549 independently of movement of blade 949. It is also understood that the circular shape of blister 549 and rotational motion is illustrative only, and that other sample vessel shapes are possible, as are non-rotational movement of the blade or rollers, such as linear, curvilinear, and semi-circular motions. Additional features of a specific embodiment of a wiper are described with reference to FIGS. 11A-B.

As discussed above, wiper 989 is provided with an x-shaped blade 949, thereby partitioning wiper into four segments 945, 946, 947, 948, as best seen in FIG. 6, and similarly dividing blister 549 into four segments 549a, 549b, 549c, and 549d, as best seen in FIG. 7. However, it is understood that this is illustrative only, and that any shape of blade 949 may be used, including a single linear blade illustratively substantially corresponding to a diameter of blister 549, a single or multiple non-linear blade including an s-shaped blade or a spiral blade, a single blade corresponding to a radius of blister 549 (similar to a clock hand), and multiple blades that divide blister 549 into multiple segments. It is understood that blades that divide blister 549 into multiple similar segments likely provide more controlled heating between different segments where entire segments will be at the annealing and denaturation temperatures at one time, whereas s-shaped, spiral, and radial blades may generate multiple vortexes, eddies, and varied mixing patterns, to move the sample across the thermal surface created by heaters 986, 987. It is also understood that less blade material allows for more of the sample to be in close contact with the heaters, while more blade material better controls fluid movement. Whatever the blade pattern, it is understood that portions of the fluid in blister 549 will be at the annealing temperature, while other portions will be at the denaturation temperature, and yet other portions may be in transition between the temperatures, all within a single sample container. The choice of shape for blade 949 may depend on size and thickness of the blister and size of the heaters, and the desirability of using wiper 989 for expelling material from blister 549 once first-stage thermal cycling has been completed.

In the illustrative embodiment, heaters 986, 987 provide a flat surface against which blister 549 may be pressed. However, it is understood that this is illustrative only, and heaters 986, 987 may provide a textured surface to aid in mixing for sample uniformity.

In the illustrative embodiment, heaters 986 and 987 are each provided at fixed temperatures, illustratively 94° C. and 60° C. respectively. However, it may be desirable to adjust the temperature of heaters 986 and 987 during use, in some embodiments. For example, it may be desirable to increase the temperature of one or both heaters when the sample is first introduced to blister 549, to compensate for a cooler temperature of the fluid as it enters blister 549. This hotter temperature may be used only when the sample is first introduced into blister 549 or may be used during the first few cycles. In another example applicable to the following discussion, it may be desirable to "overdrive" the heaters to allow the heaters to achieve the target temperature of the fluid in the blister more rapidly. For instance, if the target temperatures for thermocycling are 94° and 60°, then the heaters may be set above the high temperature (e.g., in a range of 95-110° C.) and below the lower temperature (e.g., in a range of 59-50° C.) to more rapidly heat and cool the fluid in the sample. Additionally, while two heaters are shown, any number of heaters may be used. One illustrative example uses three heaters, with one set at a denaturation temperature, one set at an annealing temperature, and the third set at an elongation temperature. In another illustrative example, a first heater may be larger than a second heater, so that the sample stays at the first temperature for a longer portion of the cycle. Moreover, it is understood that blister 549 and its contents may remain stationary, and heaters 986, 987 may be rotated or translated laterally.

Illustratively, fluid may enter blister 549 through channel 552a from a nucleic acid extraction zone, illustratively similar to blister 546 of the pouch of FIG. 1, and channel 552a may then be closed. Member 981 then presses on blister 549, promoting contact of blister 549 with heaters 986 and 987, and then blade 949 is moved toward heaters 986, 987 and divides blister 549 into segments 549a, 549b, 549c, and 549d. As wiper 989 is rotated, sample in each of the four segments 549a, 549b, 549c, and 549d is moved from contact with heater 986 to contact with heater 987, and back again. The amount of time needed to heat and cool the sample in each of the segments is dependent on a number of factors, including thickness of film on blister 549, thickness of the fluid layer within blister 549, mixing of the sample within blister 549, and/or amount of contact with the heaters. However, it is understood that one full revolution of wiper 989 generally corresponds to one cycle of PCR in this illustrative embodiment.

With certain assays, target nucleic acids may be present in very small quantities. Accordingly, it may be necessary to start with a substantial volume of sample in blister 549 in order to have enough copies of the target nucleic acid present. Illustratively, blister 549 contains about 10 µL to about 1 mL of fluid, illustratively between about 25 µL and about 200 µL, but other volumes may be appropriate depending on the configuration of the system. Optionally, after a few cycles, illustratively after 2 to 10 cycles, when the amount of target nucleic acid has been somewhat amplified, channel 552a (or another channel) may be opened, and body 913 may be moved closer to heaters 986, 987 to squeeze blister 549, thereby expelling a portion of the fluid from blister 549 through channel 552a. Channel 552a may then be closed. At least a portion of the sample may also be expelled by motion of blade 949, particularly if blade 949 may be shaped to force at least a portion of the sample outward, such as with an s-shaped blade. Illustratively, about 5%, about 10%, about 15%, about 20%, about 25%, about 30%, about 35%, about 40%, about 45%, about 50%, about 55%, about 60%, about 65%, about 70%, about 75%, about 80%, about 85%, or about 90% or more of the sample volume may be removed, or any amount or range in between. If a compressible or semi-compressible member 981 is used, it is understood that the motion of body 913 toward heaters 986, 987 may need to be adjusted to compensate for this compression to achieve the appropriate reduction in sample volume. Since the volume of fluid in blister 549 is now reduced, less time may be needed in contact with each of the heaters 986, 987 to bring the fluid to the appropriate temperature and the speed of the wiper 989 rotation may be increased, thereby reducing cycle times. Illustratively, when the sample volume is reduced by about 50%, cycling time may be reduced by about 25 to about 50%. In one example, the sample volume was reduced by about 50% and the cycling time was reduced by about 35%. After a few more cycles, an additional reduction in volume, with corresponding reduction in cycle time may take place. Multiple reductions, illustratively one to five reductions may take place. It is understood that efficient reactions essentially double the target sequence each cycle. Thus, in some embodiments, losing some portion of the sample after several of the early cycles to gain faster run time may be a good trade-off.

Figure 9A:
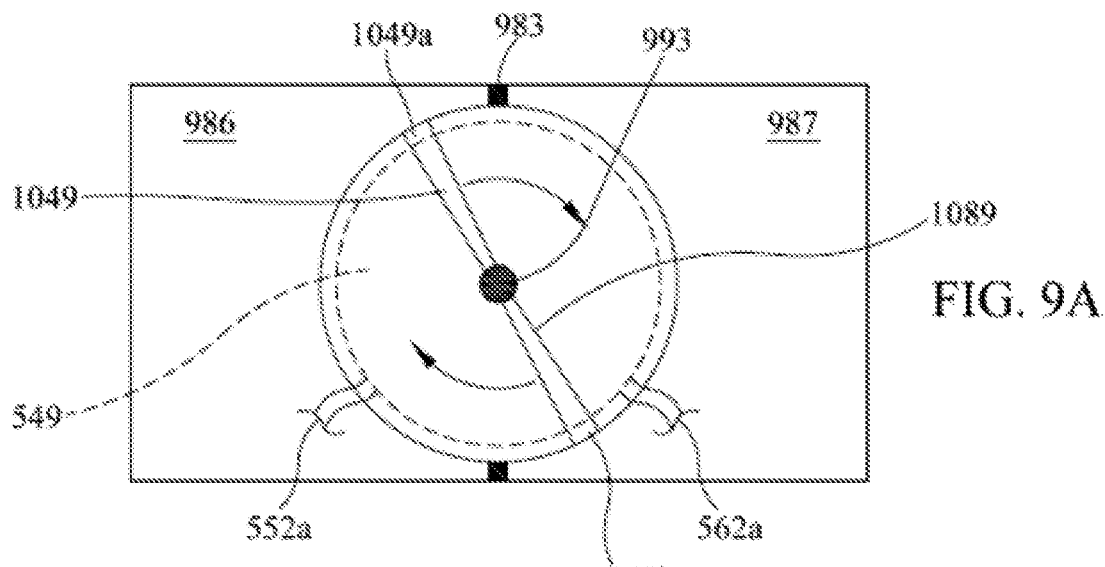
FIGS. 9A-9C are similar to FIG. 7 but showing an alternate embodiment of a wiper.
Figure 9B:
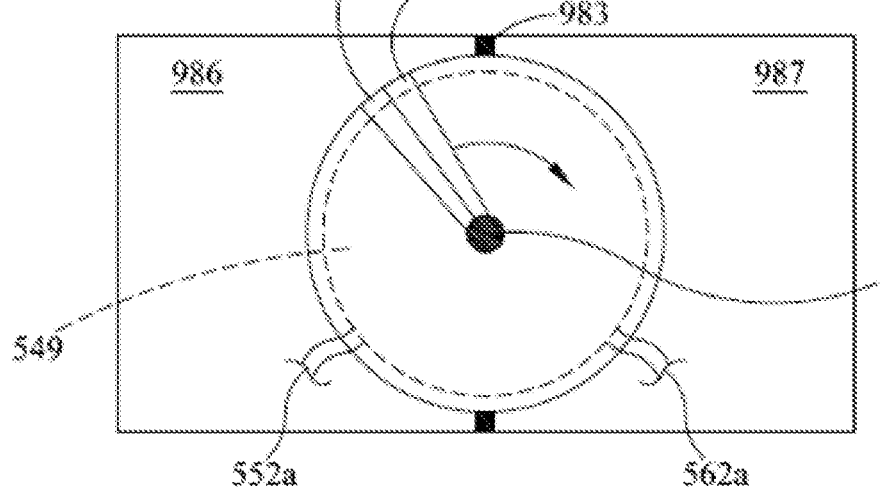
Figure 9C:
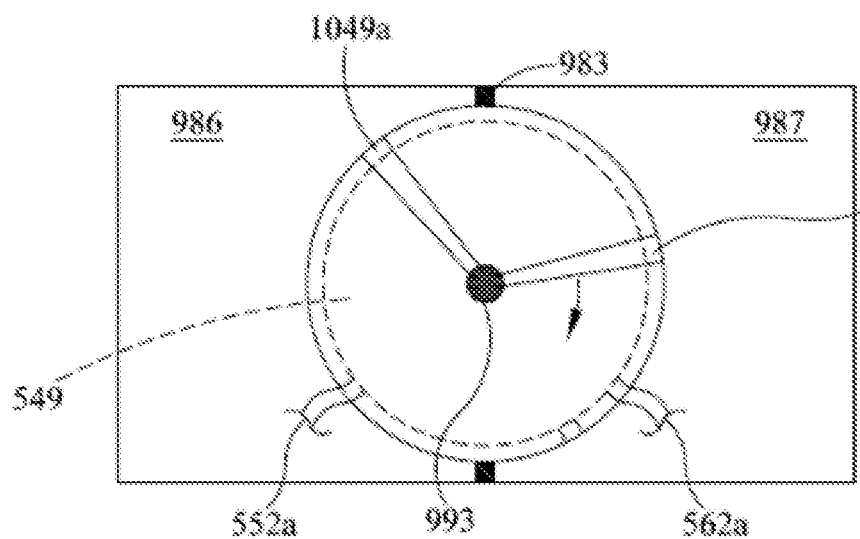

FIGS. 9a-9c show another embodiment that may be employed (e.g. to reduce the volume of sample 572 or to expel fluid from blister 549). In this embodiment, wiper 1089 is provided with blade 1049 that has two arms, 1049a and 1049b. As shown in FIG. 9a, the two arms 1049a and 1049b are provided in a linear arrangement, thus dividing blister 549 into two substantially equal halves. As shown by the arrows, blade 1049 may be moved in a clockwise direction, although, as discussed above, other motions are possible. However, in this embodiment arms 1049a and 1049b may be moved independently. To reduce the volume, arm 1049*b* may be rotated toward arm 1049*a* to reach a desired location. This movement may be made with or without moving body 913 away from heaters 986, 987. If wiper 1089 is retracted from heaters 986, 987 during this movement, body 913 may be moved back toward heaters 986, 987 after the movement is complete. Once arms 1049*a* and 1049*b* are in a desired position, as best shown in FIG. 9*b*, channel 552*a* may be opened, and blades 1049*a* and 1049*b* may be moved apart from each other, illustratively by moving blade 1049*b* in the direction shown by the arrow in FIG. 9*b* to get to the position in FIG. 9*c*. While about 100 degrees of rotation is shown in FIG. 9*c*, this is illustrative only, and the amount of rotation may be adjusted to achieve the appropriate reduction in volume or emptying of the blister. It is understood that one or both of arms 1049*a* and 1049*b* may be moved to achieve this reduction in volume. Channel 552*a* may then be sealed, arms 1049*a* and 1049*b* may be moved back to their linear arrangement, and thermocycling may continue.

It is understood that sample volume reduction after a few cycles along with reductions in cycle time may be used with any of the embodiments disclosed herein or with other embodiments using a wide variety of sample vessels and heating configurations. In addition to reducing cycle time when the sample volume is reduced, it is understood that different annealing and/or denaturation temperatures may be used with different cycles, as discussed in Example 2.

It is also understood that this method of reducing volume and decreasing cycle time may be combined with the introduction of fresh PCR components. Such may be useful when a combined RT-PCR reaction is desired or where such addition may include primers for nested amplification or for use with universal primers. Other embodiments are possible.

Once thermal cycling is complete, channel 562*a* may be opened. Illustratively, particularly when blade 949 is curved the direction of wiper 989 may be used to pump fluid from blister 549 into channel 562*a*. Alternatively, blister 549 may be a stand-alone container for thermocycling a sample, such that blister 549 is sealed after receiving a PCR reaction. Blister 549 may be used for any of a variety of sample types that require thermocycling.

Figure 10:
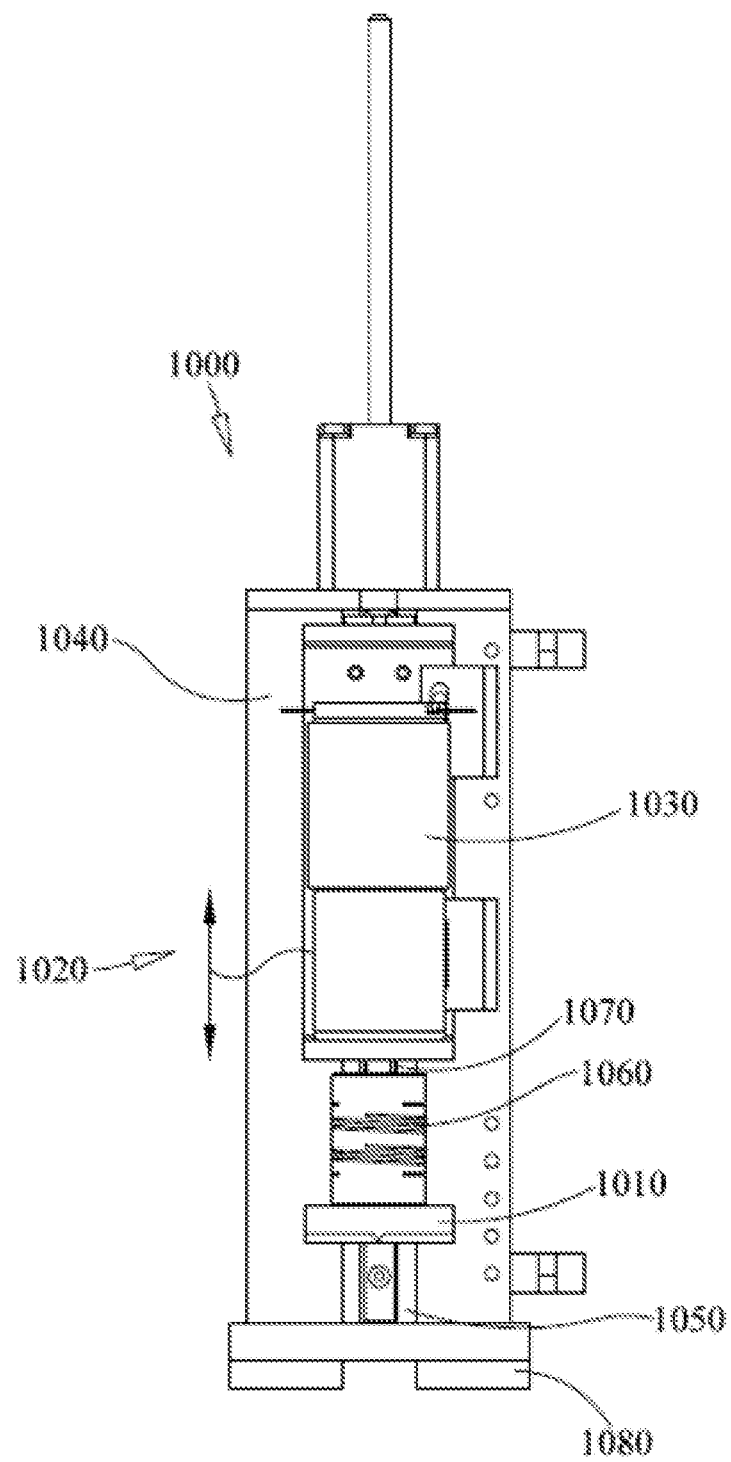
FIG. 10 illustrates an embodiment of a wiper system that can be used with the thermocycling embodiments illustrated in FIGS. 6-9C.

FIG. 10 illustrates an embodiment of a wiper system 1000 that can be used with the heater devices illustrated in FIGS. 6-9C for, for example, moving the contents of a blister between two heat zones for thermocycling. The wiper system 1000 includes a wiper head 1010 that may be attached to a rotary motor 1030 via shaft 1070 and connector 1060. Rotary motor 1030 may be coupled to support 1040; motor 1030 and wiper head 1010 can be raised and lowered as indicated by arrows 1020 on support 1040 on, for example, rail 1050. Wiper system 1000 may be mounted above heaters 986, 987 (shown in FIGS. 6-7), with space for a sample blister to be inserted therebetween.

In one embodiment, wiper system 1000 may be mounted in an instrument such that a blister in a sample vessel may be placed below base 1080. In one example, the head 1010 and motor 1030 assembly may be lowered past the base 1080 to contact a fluid-filled blister. Motor 1030 can be rotated so that the wiper head 1010 can move the contents of the fluid-filled blister. If the fluid-filled blister is in contact with a heater device (e.g., heaters 986 and 987) having separate heated zones (e.g., a zone at 94° C. and a separate zone at 60° C.), the motor 1030 and wiper head 1010 can be lowered so that the blade(s) of the wiper head 1010 divide the blister into separate, discrete volumes and used to move the contents of the fluid-filled blister for thermal cycling for PCR, as described above in reference to FIGS. 6-9C.

In addition to the thermal cycling devices described above, the heater and mixer systems described herein can also be used for automated sample preparation in an enclosed pouch. For instance, as will be described in greater detail below, heating a blister like 549 with one or both of heaters 986 and 987 while blending the contents of a sample preparation blister with mixer system 1000 can be used to lyse cells (e.g., bacterial and mammalian cells) and release the nucleic acids therein. Alternatively, or in addition, a blister may include a chaotropic agent, a detergent, and/or lysis beads (see, e.g., lysis blister 522 of pouch 510 of FIG. 1). Likewise, heating and cooling with thermoelectric heating and cooling devices (i.e., Peltier devices) and mixing can be used to increase the efficiency of other sample preparation processes. For example, nucleic acids bind more efficiently to magnetic beads (e.g., magnetic beads 533 of FIG. 1) at lower temperatures (e.g., ~0-10° C.) and are eluted more efficiently from the magnetic beads at higher temperatures (e.g., ~60-90° C.). Thus, lysing may illustratively occur when blister 549 is in contact with heater/cooler 986, while magnetic bead binding may illustratively occur when blister 549 is in contact with heater/cooler 987, and these heaters may move laterally, as discussed below with respect to FIGS. 12-13.

Figure 11B:
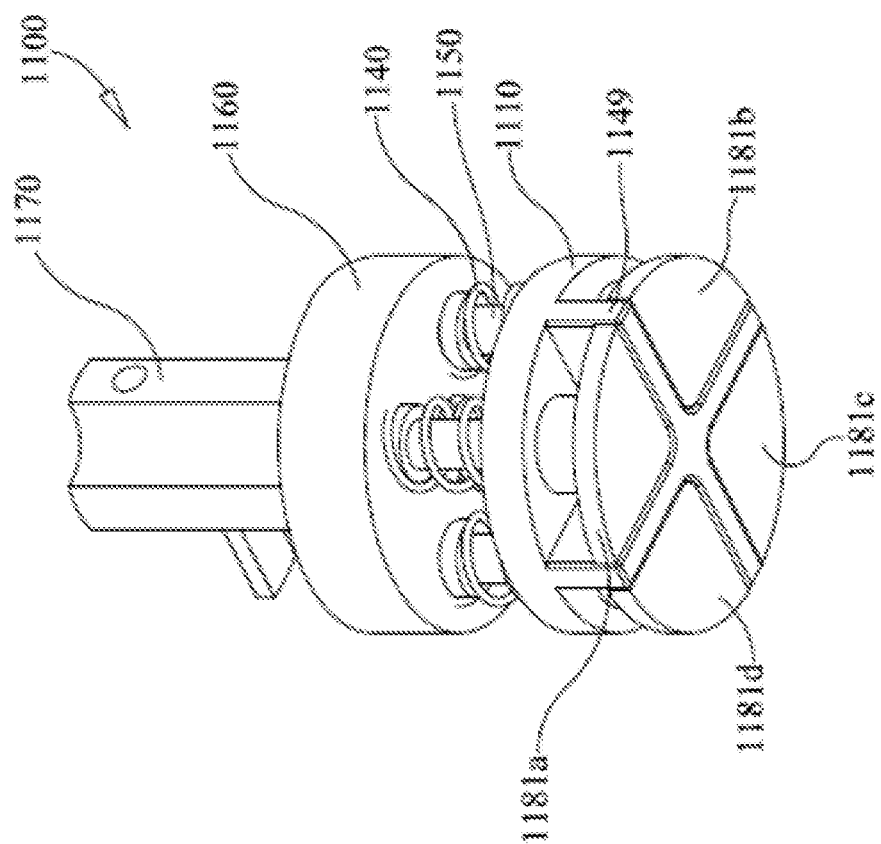
FIGS. 11A and 11B illustrate a wiper head according to one embodiment of the present disclosure.
Figure 11A:
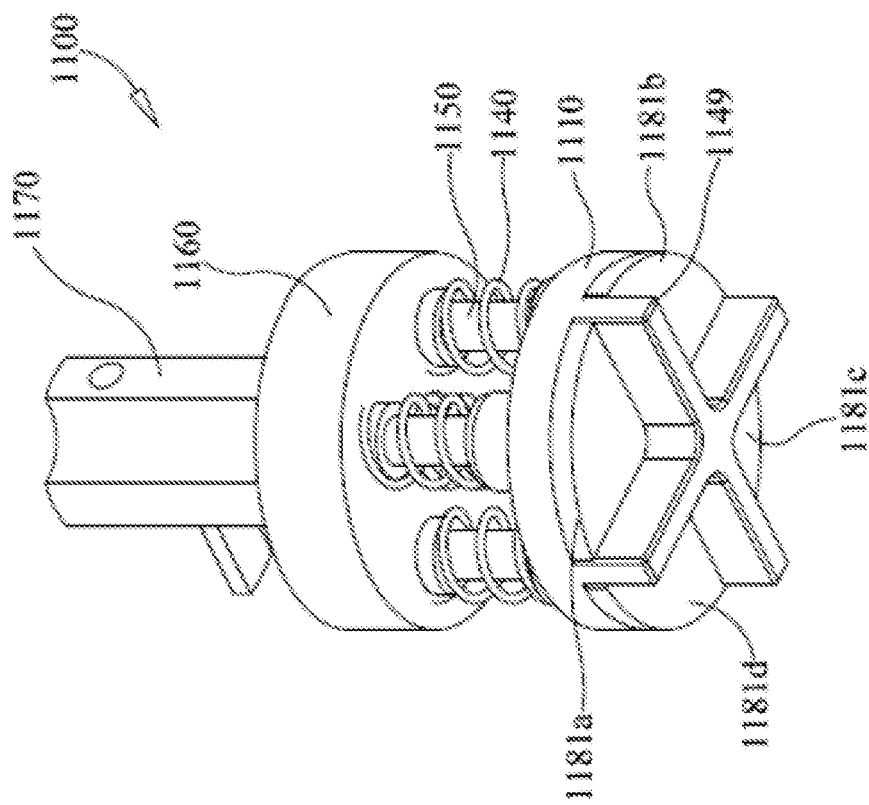

Referring now to FIGS. 11A and 11B, an embodiment of a wiper head 1100 that may be included on the wiper system of FIG. 10 is illustrated. The wiper head 1100 may, for instance, be attached to the shaft 1070 of the wiper system 1000 of FIG. 10 via the chuck 1170 that is at the distal end of the wiper head. The proximal end of the wiper head 1100 includes a wiper body 1110 with wiper blades 1149. The wiper head 1100 may also include spring members 1140, and a pins, screws, or the like 1150 that couple the upper portion of an upper body 1160 to the wiper body 1110. In one embodiment, the wiper head may be configured such that the spring members 1140 can regulate the amount pressure that the wiper head 1110 and wiper blade 1149 can exert on a fluid-filled blister.

The illustrated wiper body 1110 may also illustratively include pressure members 1181*a*-1181*d* that are disposed in the quadrants between the wiper blades 1149. In one embodiment, the pressure members 1181*a*-1181*d* may work together to function like pressure member 981 described in relation to FIGS. 8A-8D. That is, pressure members 1181*a*-1181*d* may be positioned relative to the wiper blades 1149 such that the pressure members 1181*a*-1181*d* can apply a consistent, predictable pressure when the wiper blades 1149 are brought into contact with a fluid-filled blister. However, in reference to FIG. 11B, another embodiment is illustrated where the pressure members 1181*a*-1181*d* may be deployed, moved, or lowered relative to the wiper blades 1149 to apply pressure to a fluid filled blister. In the illustrated example, the pressure members 1181*a*-1181*d* may be deployed by lowering the wiper head 1100 until the blades 1149 and the pressure members 1181*a*-1181*d* present a substantially flat surface against the fluid filled blister. In one embodiment, the pressure members 1181*a*-1181*d* may be deployed by lowering the wiper head 1100 past the point that the wiper blades 1149 contact the blister; continuing to lower the wiper head 1100 can compress the wiper blades 1149 up and/or press the pressure members 1181*a*-1181*d* down. The spring members 1140 may be configured to regulate the amount of pressure on the blades 1149 and the plunger head 1110 is needed to deploy the pressure members. Lowering the wiper head 1100 down until the wiper blades and the pressure members form a substantially planar surface may, for instance, be used to spread liquid uniformly within a blister or to plunge liquid from one blister to another. In another embodiment (not shown), the pressure members may be deployed to an intermediate position by a similar mechanism to, for example, exert pressure on a fluid-filled blister to improve contact between the blister and an underlying heater. In one or more embodiments, the wiper head 1100 may include multiple spring member types associated with the wiper blade(s) 1149 and/or the pressure members 1181a-1181d to modulate or regulate the amount of pressure that the blades 1149 and the pressure members 1181a-1181d can apply to a fluid-filled blister.

Figure 12A:
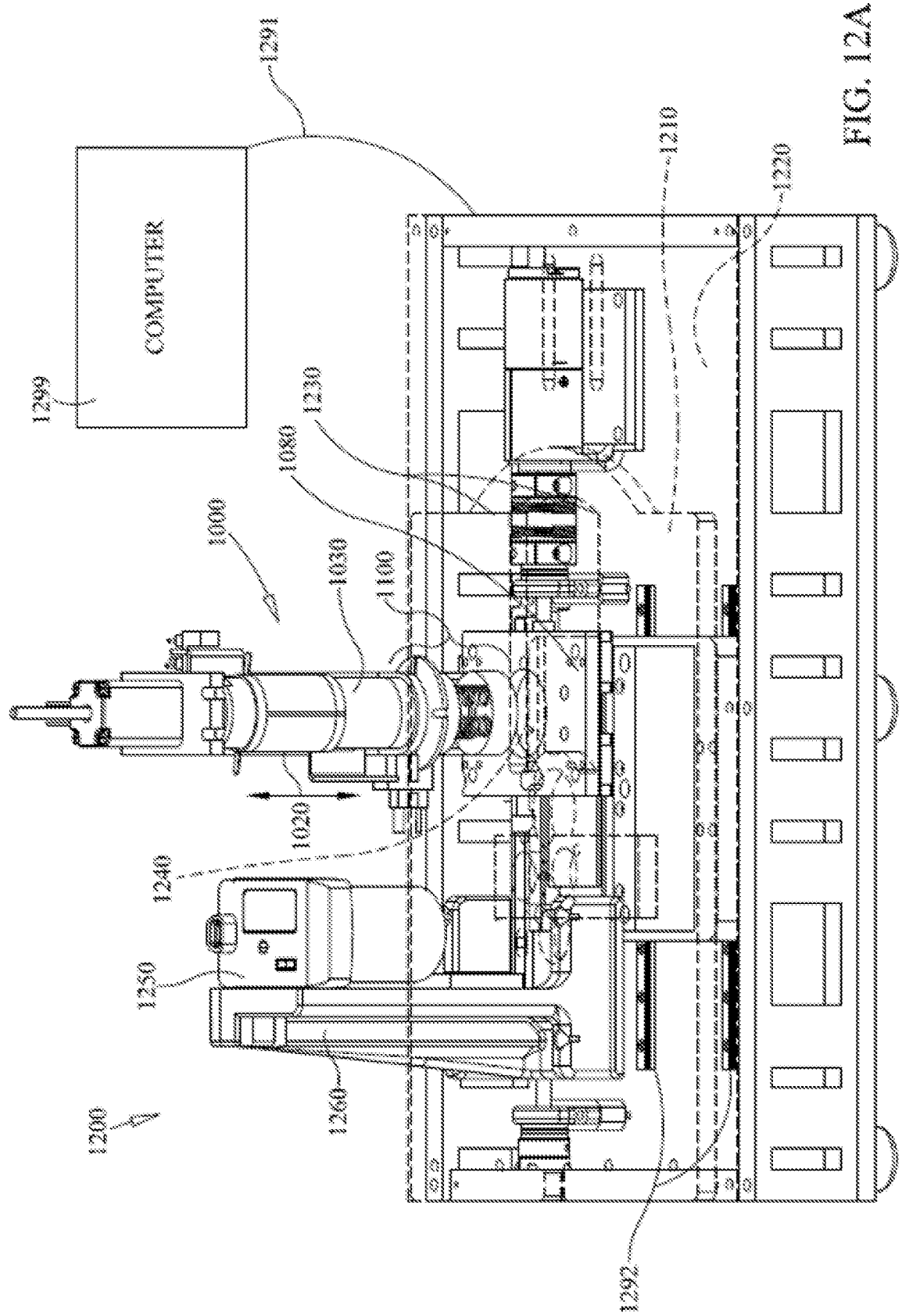
FIGS. 12A and 12B illustrate a thermocycling instrument that incorporates a wiper system and a heater that includes at least two temperature zones, according to one embodiment of the present disclosure.
Figure 12B:
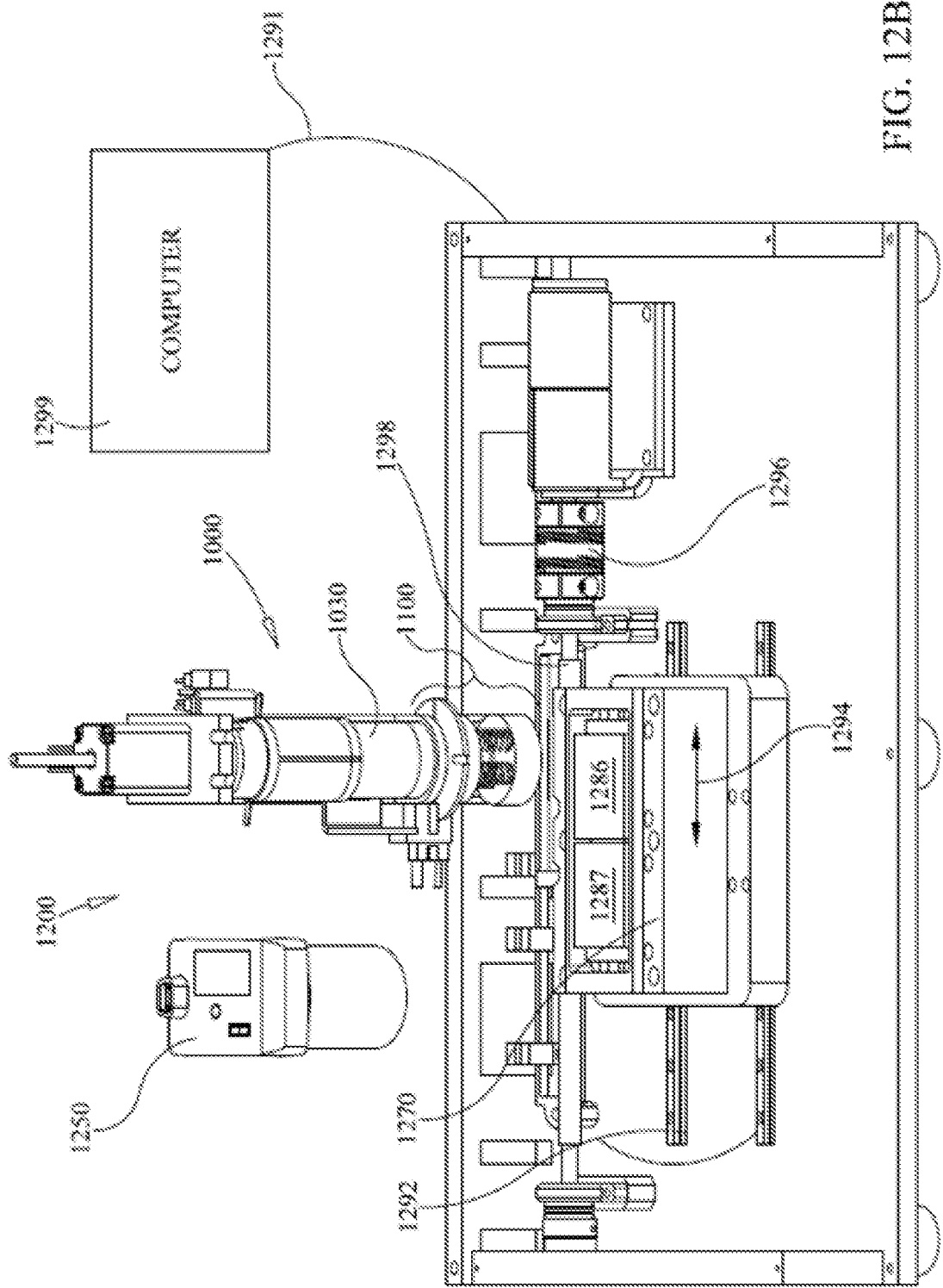

Referring now to FIGS. 12A and 12B, an instrument 1200 is illustrated that includes features of the wiper system 1000 discussed in reference to FIG. 10, the wiper head 1100 discussed in reference to FIGS. 11A and 11B, and many of the features of the heaters 986 and 987 of FIG. 6. In the illustrative example, the instrument 1200 includes a hinged cover 1210 and a chassis cover 1220. The hinged cover 1210 can be opened for insertion of a flexible pouch for self-contained PCR into the instrument between the hinged cover 1210 and the chassis cover 1220. The chassis cover 1220 lies over the internal components of the instrument 1200 and may define a receptacle for positioning a flexible pouch such as the one illustrated in FIG. 14A in the instrument, wherein the receptacle may be coextensive with a portion of the pouch. As will be explained in greater detail below, the receptacle may be configured to receive the flexible pouch in the instrument and align the flexible pouch so that various components of the instrument can interact with the flexible pouch. Likewise, the receptacle may include openings and the like so that the internal components of the instrument can contact the flexible container. Likewise, the hinged cover 1210 may include openings and the like so that external components of the instrument can interact with the flexible container. Above the covers 1210 and 1220, the instrument 1200 includes the wiper system 1000, which includes the drive motor 1030 and the wiper head that were previously described, and camera/fluorimeter 1250 and a mount 1260 for collection of fluorimetric data. As in the previous examples, the wiper system can be moved up and down as indicated by arrows 1020 through a hole 1240 in the base 1080 and through one or more holes in the hinged cover 1210 in order to contact the pouch.

In addition, in the illustrated embodiment, the wiper system may be translated side-to-side, illustratively on rails 1230, so that the wiper system 1000 can contact different regions of a pouch inserted into the instrument 1200. In one embodiment, the wiper system 1000 may be translated so that the wiper 1100 can interact with different portions of the pouch. For instance, as will be explained in greater detail below, the wiper system 1000 may be used for in-pouch sample preparation and first-stage PCR steps. In an alternative embodiment, the wiper system 1000 may be held stationary and the pouch may be moved so that the wiper can contact different portions of the pouch. It is understood, however, that this arrangement is illustrative, and other arrangements of moving and aligning wipers, heaters, and sample containers are contemplated. It is understood that any combination of wipers, heaters, and pouches may be placed on movable elements and that when translation of wipers, heaters, pouches, and the like is discussed, such movement may be replaced with opposite translation of the wiper, heater, or pouch, working in concert with that element, in any embodiment where such opposite translation is consistent with the arrangement of other elements. In some embodiments, rotary motion of the pouch and other instrument elements is also contemplated.

Referring now specifically to FIG. 12B, the covers 1210 and 1220 are removed so that the interior of the instrument 1200 can be seen more clearly. The interior of the instrument 1200 illustratively includes a heater assembly 1270 that can be translated back and forth by a translator as shown by arrow 1294, for example, on rails 1292. The heater assembly 1270 includes a first heater element 1286 and a second heater element 1287. In the illustrated embodiment, the heater assembly may be mechanically coupled to a translator that illustratively includes a drive motor 1296 and drive member (e.g., a threaded screw) 1298. Heater assembly 1270 may be translated back and forth, for example, on rails 1292 so that the heaters 1286 and 1287 can interact with different regions of a pouch installed in the instrument. However, it is understood that a motor and rails are illustrative only, and that other linear and non-linear translators may be used. As was discussed in detail above in reference to FIGS. 6-9C, the heater assembly may be positioned so that portions of a blister (e.g., a first-stage PCR blister) can be under temperature control of first heater element 1286 and a second heater element 1287 at the same time, similar to that shown in FIGS. 6-8. Likewise, an entire blister may be controlled by one heater at a time, and the blister (e.g., a first-stage PCR blister or a second-stage PCR blister) can be thermocycled by moving the heater assembly 1270 back and forth with the translator so that a selected blister is repeatedly under temperature control of the first heater 1286 and then the second heater 1287, etc. One will appreciate that while the illustrated embodiment includes a heater that can move, the same effect(s) can be accomplished by translating the pouch relative to the heaters instead of moving the heater assembly and that this motion can be along linear, arcilinear, or rotational paths, for example.

In one embodiment, one or both of heaters 1286 and 1287 may include a Peltier element. While heaters 1286 and 1287 may not be thermocycled, it may, for instance, be desirable to include a Peltier element in one or both of heater 1286 and 1287. Unlike a typical resistance heater, Peltier elements can actively cool as well as heat samples. For example, in moving a sample from a denaturation temperature (e.g., 94° C.) to an annealing temperature (e.g., 60° C.), the sample has to be cooled down to the annealing temperature. This will happen by radiation/conduction, but these processes are relatively slow. For rapid thermocycling, it may be preferable, for example, to actively cool the sample with Peltier device with the "cool" side of the Peltier set to 60° C. and the "hot" side, where excess heat may illustratively be pumped and disposed of through a heat sink, may be set to a higher temperature.

Instrument 1200 also includes a computer (or other computing device) 1299 that may be configured to control one or more of the wiper 1100, the heaters 1286 and 1287, thermocycling parameters (e.g., movement of the wiper, temperatures of the heaters, alignment of the wiper and heaters with the sample container, etc.), fluid movement in the sample container, etc. Likewise, the computer 1299 may be configured for data acquisition and analysis from the instrument 1200, such as from optical system 1250. Each of these components is connected electrically, illustratively via cable 1291, although other physical or wireless connections are within the scope of this invention. It is understood that computer 1299 may be housed within instrument 1200 or may be external to instrument 1200. Further, computer 1299 may include built-in circuit boards that control some or all of the components, and may also include an external computer, such as a desktop or laptop PC or smartphone, to receive and display data from the instrument 1200. An interface, illustratively a keyboard interface, may be provided including keys for inputting information and variables such as temperatures, cycle times, etc. Illustratively, a display may also be provided. The display may be an LED, LCD, or other such display, for example.

Figure 13A:
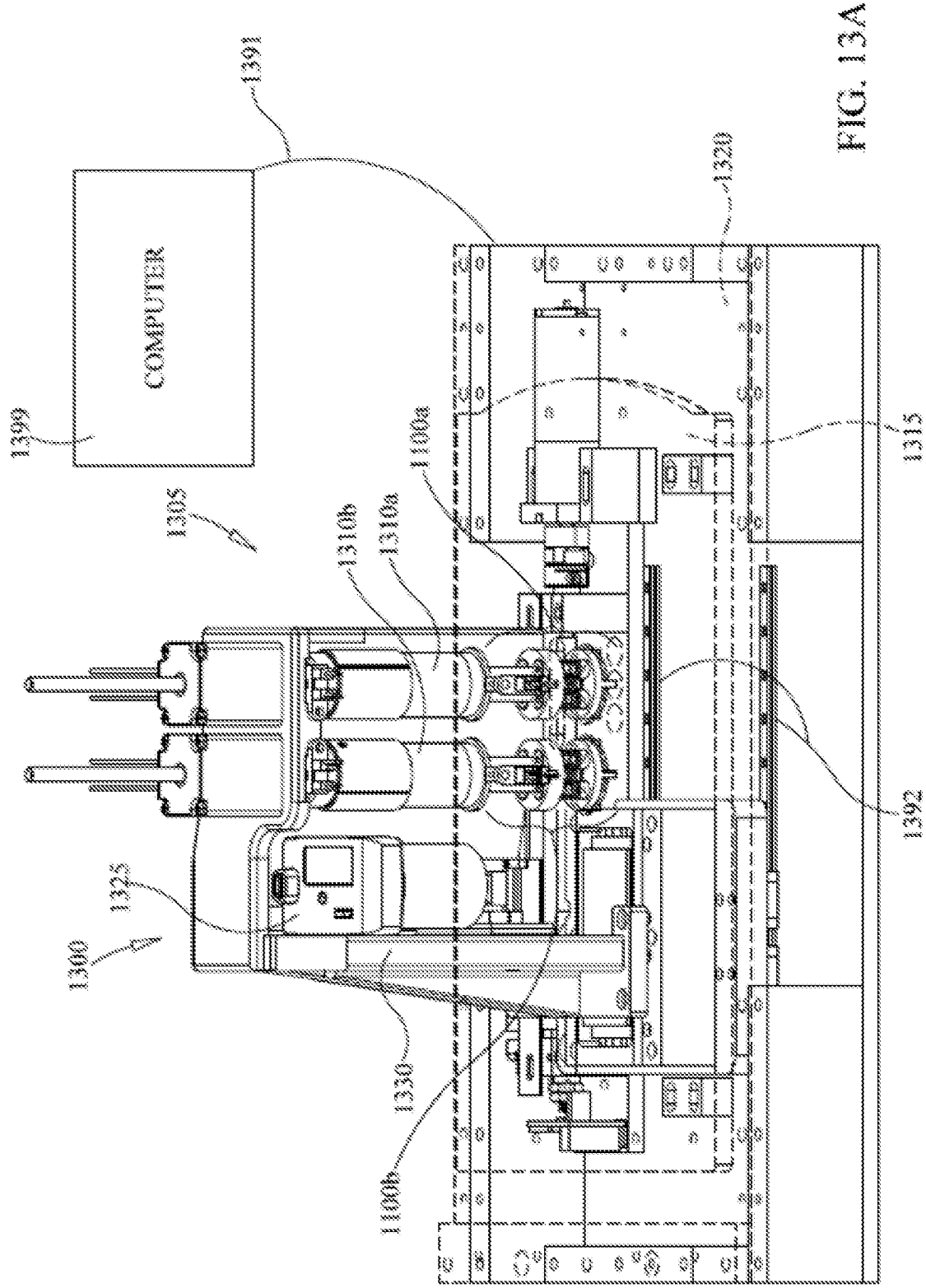
FIGS. 13A and 13B illustrate another thermocycling instrument that incorporates a wiper system and a heater that includes at least two temperature zones, according to one embodiment of the present disclosure.
Figure 13B:
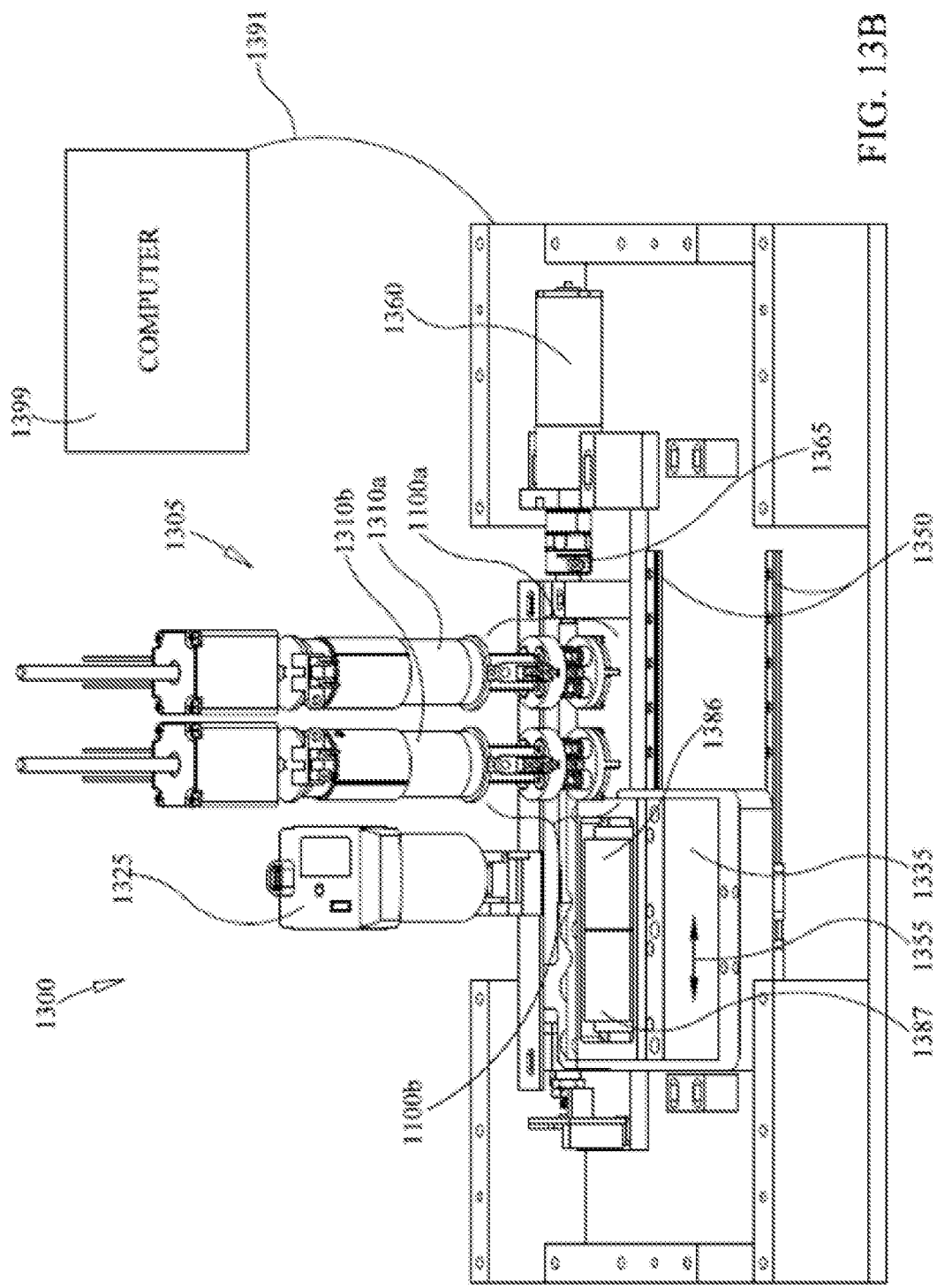

Referring now to FIGS. 13A and 13B, another instrument 1300 is illustrated. Instrument 1300 is substantially similar in many respects to instrument 1200, except instrument 1300 includes a wiper system 1305 with two mixer/wipers. Thus, in one embodiment, there may be no need to translate the wipers horizontally so that the wiper/mixer can interact with different portions of a pouch installed in the instrument 1300.

The instrument 1300 includes the wiper system 1305, which includes first and second wiper motors 1310a and 1310b and first and second wiper heads 1100a and 1100b. The instrument also includes first and second covers 1315 and 1320, a camera 1325 and a camera support 1330. Referring now to FIG. 13B, the instrument 1300 further includes a heater system 1335 that can be translated horizontally 1355 on rails 1350, and first and second heater elements 1386 and 1387. While the term "heater" is used to refer to elements 1386 and 1387, it is understood that other temperature control elements or combinations of elements may be used to adjust the temperature of the sample. The heater system 1335 is mechanically coupled to a drive motor 1360 and a drive member 1365 for translation of the heater system. Illustratively, heater 1386 may be provided at a temperature in a range of about 90-95° C. and heater 1387 may be provided at a temperature in a range of about 55-65° C., although other temperatures and arrangements are possible.

Instrument 1300 also includes a computer (or other computing device) 1399 that may be configured to control one or more of the wipers 1100a and 1100b, the heaters 1386 and 1387, thermocycling parameters (e.g., movement of the wiper, temperatures of the heaters, alignment of the wiper and heaters with the sample container, etc.), fluid movement in the sample container, etc. Likewise, the computer 1399 may be configured for data acquisition and analysis from the instrument 1300, such as from optical system 1325. Each of these components is connected electrically, illustratively via cable 1399, although other physical or wireless connections are within the scope of this invention. It is understood that computer 1399 may be housed within instrument 1300 or may be external to instrument 1300. Further, computer 1399 may include built-in circuit boards that control some or all of the components, and may also include an external computer, such as a desktop or laptop PC, to receive and display data from the instrument 1300. An interface, illustratively a keyboard interface, may be provided including keys for inputting information and variables such as temperatures, cycle times, etc. Illustratively, a display may also be provided. The display may be an LED, LCD, or other such display, for example.

Figure 14B:
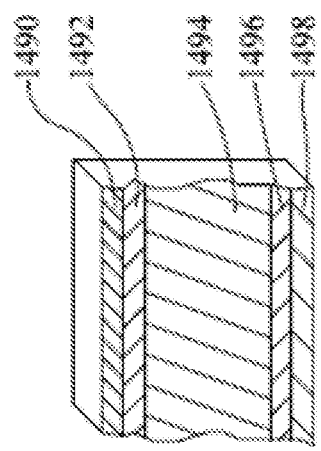
FIG. 14B shows a partial cross-sectional view of the pouch of 14A along the line B-B.
Figure 14A:
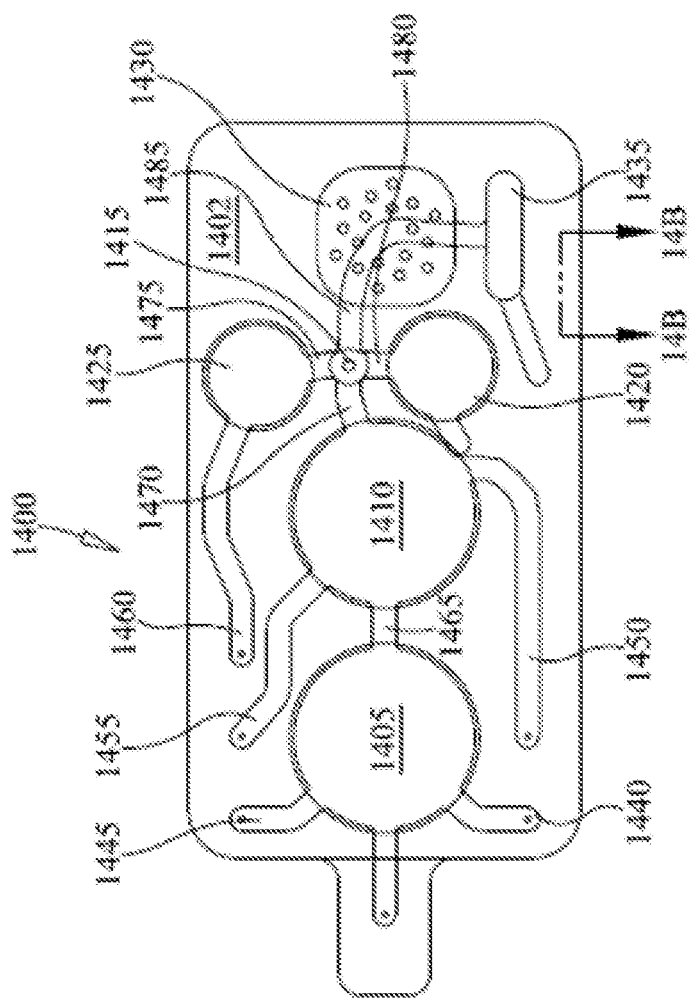
FIG. 14A shows a flexible pouch useful for self-contained PCR.

Referring now to FIGS. 14A and 14B, an embodiment of a flexible pouch or chemistry card that may be used in instruments 1200 and 1300 is described. The illustrative flexible pouch 1400 of FIG. 14A comprises a substantially planar region 1402 that includes a number of zones or blisters where sample preparation, nucleic acid amplification, and detection can occur. In one embodiment, the pouch 1400 may be fabricated from a number of layers of material (layers of the same material or layers of different types of material) that are sealed together to form the pouch 1400. In FIG. 14B a cutaway illustrating the layers along the line B-B is shown. The illustrative pouch includes a first film layer 1490, a pressure sensitive adhesive layer 1492, a card layer 1494, a second pressure sensitive adhesive layer 1496, and a second film layer 1498. In one illustrative example, the blister areas in the pouch 1400 can be formed by making appropriate cutouts in the card layer 1494. Alternatively, the blister areas of the pouch can be formed by laminating or welding film layers (e.g., film layers 1490 and 1498) together leaving open spaces between the layers that serve as liquid blisters with or without the card layer. One will appreciate that other configurations are possible. It is understood that while the illustrative blister areas are flexible, the card layer 1494 optionally may be less flexible and may be rigid, and still be part of a flexible sample container. Thus, it is understood that a "flexible pouch" need only be flexible in certain zones. Fill channels 1440-1460 and channels connecting the blister areas 1465-1485 may be formed by making appropriate cutouts in the either the first or second pressure sensitive adhesive layers 1492 and 1496, or by providing channels in the card layer 1494. Alternatively, or in addition, flow channels between the blister areas can be formed by adding another film layer above film layer 1490 or below film layer 1498 and welding the layers together, leaving open blister areas and channels between the layers.

While other materials may be used, illustratively, the film layers of pouch 1400 may be formed from a flexible plastic film or other flexible material similar to the pouch 510 described in FIG. 1. For instance, pouch 1400 may be fabricated from materials such as, but not limited to, such as polyester, polyethylene terephthalate (PET), polycarbonate, polypropylene, polymethylmethacrylate, combinations, mixtures, and laminated layers thereof that can be made by any process known in the art, including extrusion, plasma deposition, and lamination. Similar materials (e.g., polycarbonate) may be used for the card layer 1494. Other materials, including metal foils or plastics with aluminum lamination, may also be used. Other barrier materials are known in the art that can be sealed together to form the blisters and channels. If plastic film may be used, the layers may be bonded together, illustratively by heat sealing. Illustratively, the material has low nucleic acid binding capacity. If fluorescence detection is used, optically transparent material may be used in the appropriate areas of the pouch (e.g., in the vicinity of the second-stage array).

Turning back to FIG. 14A, the illustrative pouch 1400 includes a sample preparation blister 1405 where a sample containing nucleic acids to be amplified and analyzed is introduced into the pouch 1400. The pouch further includes a first-stage PCR blister 1410, a volumetric well 1415 for measuring a portion of the product from first-stage PCR prior to second-stage PCR, and an array of reaction wells 1430 for second-stage PCR. The volumetric well 1415 may also be fluidly coupled to a reagent blister 1425, where reagents for second-stage PCR are introduced, and a mixing blister 1420. A sample for second-stage PCR may be prepared by repeatedly mixing the contents of volumetric well 1415 between blisters 1420 and 1425. The second-stage array 1430 may also be fluidly connected to a waste receptacle 1435. Alternatively, blister 1410 may be used for both sample preparation and first-stage PCR and blister 1405 may be used as a waste receptacle for, for example, sample preparation waste(s). Means for introducing sample and reagents into the pouch 1400 are not illustrated in FIG. 14A, but one will appreciate that a device similar in form to fitment 590 of FIG. 1 can be fitted to pouch 1400 and used for introduction of sample and reagents into the pouch 1400. Likewise, a sealable port (not shown) may be provided for introduction of sample into the pouch 1400 and one or more sealable ports may be provided for introduction of a liquid reagent or a hydration buffer. In addition, the pouch 1400 may include dehydrated (e.g., freeze dried) reagents in a fitment or a similar structure that may be hydrated with a suitable hydration buffer prior to use of the pouch. It is understood that pouch 1400 is illustrative only, and that other configurations are possible, illustratively provided with liquid or dried reagents. See, e.g., WO2019/045807 for additional illustrative embodiments.

Referring still to FIG. 14A, two alternative sequences for filling the pouch, preparing a sample, performing first-stage PCR, and performing second-stage PCR are described. In a first method, sample preparation and first-stage PCR are performed in separate blisters. This is referred to herein as the "three zone method." In a first step, a sample is injected into blister 1405 via fill channel 1440. In one embodiment, cells, viruses, and the like are lysed in blister 1405 using any of the wiping systems described in detail elsewhere herein. Alternatively, cell lysis may be accomplished with an alternative lysis device such as, but not limited to, a sonication device or a bead beater or by chemical lysis. Lysis may be aided by heating the sample (e.g., to about 70-90° C.) with one or more heater elements of the heater assembly described in detail elsewhere herein. Following lysis, the sample may be cooled with a thermoelectric cooler element (i.e., a Peltier element) to a temperature in a range of about 0° C. to about 20° C. (e.g., about 10-15° C.) to aid in binding to magnetic beads. Other cooler elements include, but are not limited to, fluid or gas heat exchange elements, fan cooled heat sinks, heat pipes, condensation units, and the like.

Magnetic beads may be injected into blister 1405 via fill channel 1440 in order to recover nucleic acids from the lysate, which may be prior to or subsequent to lysis. Illustratively, the magnetic beads and the lysate may be mixed cold (e.g., in a range of about 0-10° C., illustratively by adjusting the temperature of one of the heaters). Once the magnetic beads and the lysate have been thoroughly mixed for a sufficient time, the magnetic beads may be gathered in blister 1405 with a magnet illustratively provided in the instrument and the spent lysate may be sent to liquid waste via channel 1445. Then wash buffer may be injected via fill channel 1440. The wash buffer and the magnetic beads may be mixed cold (e.g., in a range of about 0-10° C.). The magnetic beads may be gathered again and the spent wash buffer may be flushed to liquid waste via channel 1445. The wash cycle may be repeated at least one more time. Following the wash, elution buffer (plus first-stage PCR primers) may be injected into blister 1405 via fill channel 1440. The elution buffer (plus first-stage PCR primers) and the magnetic beads may be mixed hot (e.g., at about 70-90° C.), illustratively, under control of one or more heaters.

For first-stage PCR, PCR master mix (e.g., a polymerase, dNTPs, and other amplification components known in the art) may be injected into blister 1410 via fill channel 1450. The PCR master mix may be heated (e.g., to about 57° C.) prior to introduction of the eluate from the magnetic beads. In blister 1405, the magnetic beads may be gathered again and the eluate may be sent to blister 1410 via channel 1465.

First-stage PCR may be performed in blister 1410 with rotary movement with blister 1410 under temperature control of two heaters as described in detail elsewhere herein. Alternatively, first-stage PCR thermocycling may be performed by translating the heater assembly or the pouch 1400 so that blister 1410 may be under control of one heater and then another. The channels into and out of blister 1410 are closed, illustratively with hard seals, during first stage PCR.

In some embodiments, it may be possible to speed up first-stage PCR in the pouch by employing a sample volume reduction protocol. For instance, a sample volume reduction protocol may include performing several cycles (e.g., 2-10) of PCR with an initial volume (e.g., ~50 to 200 μL) in blister 1410, purging some of the volume of blister 1410, and performing more cycles of PCR. Sample volume reduction can reduce the cycle time for a PCR reaction because smaller volumes of liquid have less thermal mass and can be thermocycled more quickly than larger volumes. In addition to reducing cycle time when the sample volume is reduced, it is understood that different annealing and/or denaturation temperatures and hold times may be used with different cycles, as discussed in Example 2.

Following a sufficient number of cycles of first-stage PCR (e.g., 20-30 cycles), a small sample (e.g., ~1-5 μL) of first-stage PCR may be sent to dilution well 1415. Channel 1470 may be opened; channels 1475-1485 are closed. The sample for second-stage PCR may be prepared by injecting the second-stage PCR master mix into blister 1425 via channel 1460. Seals are closed on channels 1470 and 1485; seals are opened on channels 1475 and 1480. Blisters 1420 and 1425 and well 1415 may be heated. The sample in well 1415 may be mixed with the master mix by mixing between blisters 1425 and 1420 and well 1415 to dilute first-stage PCR product for second-stage PCR. Channel 1485 is then opened so that the second-stage PCR mix can be transferred into the second-stage PCR array 1430. In another embodiment, the pouch 1400 may include one or more additional dilution wells and sets of mixing blisters downstream from well 1415 and blisters 1425 and 1420 and upstream from array 1430. For example, in some embodiments with concentrated first-stage PCR primers or with highly concentrated product, it may be desirable to dilute the first-stage primers and product to a degree greater than can be achieved with one dilution well. The mixture for second-stage PCR may be heated for a physical 'hot-start' prior to injection into the second-stage PCR array 1430. Thermocycling for second-stage PCR in array 1430 may illustratively be accomplished by translating the heater assembly back and forth as previously described.

In the second method, sample preparation and first-stage PCR are performed in the same blister. This is referred to herein as the "two zone method." In a first step, a sample may be injected into blister 1410 via fill channel 1450. In one embodiment, cells, viruses, and the like are lysed in blister 1410 using the wiping system described in detail elsewhere herein. Alternatively, cell lysis may be accomplished with an alternative lysis device such as, but not limited to, a sonication device or a bead beater or chemical lysis. Lysis may be aided by heating the sample to an elevated temperature (e.g., about 70-90° C.) with one or more heater elements of the heater assembly described in detail elsewhere herein. Following lysis, the sample may optionally be cooled with a thermoelectric cooler element (i.e., a Peltier element) to a reduced temperature (e.g., a temperature below ambient temperature such as, but not limited to, ~0-10° C.).

Magnetic beads may be injected into blister 1410 via fill channel 1450 in order to recover nucleic acids from the lysate. Magnetic beads are injected into blister 1410 via fill channel 1450. The magnetic beads and the lysate may be mixed cold (e.g., at a temperature in a range of about 0-10° C.). Once the magnetic beads and the lysate have been thoroughly mixed for a sufficient time, the magnetic beads may be gathered in blister 1410 with a magnet and the spent lysate may be sent to blister 1405 (i.e., the liquid waste blister in this example) via channel 1465. Then wash buffer may be injected into blister 1410 via fill channel 1450. The wash buffer and the magnetic beads may be mixed cold (e.g., at a temperature in a range of about 0-10° C.). The magnetic beads are gathered again and the spent wash buffer may be flushed to blister 1405. The wash cycle may be repeated one or more times, if desired. The magnetic beads may be collected into the upstream half of blister 1410, and sent to waste blister 1405 via channel 1465.

For first-stage PCR, the wiper system may be set and elution buffer (plus primers) may be injected into channel 1450 and may be held at an elevated temperature (e.g., about 57° C.). At the same time, first-stage PCR master mix may be injected into channel 1455 and optionally held at an elevated temperature (e.g., about 57° C.) if a true hot-start may be desired. First-stage PCR master mix may be mixed with primers and template in blister 1410 and first-stage PCR may be performed as described above.

Following first-stage PCR, the magnetic beads are gathered and in embodiments where dilution is desired, a small sample (e.g., 1-5 μL) of the first-stage PCR product may be transferred to the dilution well 1415. Channel 1470 is opened; channels 1475-1485 are closed. The sample for second-stage PCR may be prepared by injecting the second-stage PCR master mix into blister 1425 via channel 1460. Seals are closed on channels 1470 and 1485; seals are opened on channels 1475 and 1480. Blisters 1420 and 1425 and well 1415 are heated. The sample in well 1415 may be mixed with the master mix by mixing between blisters 1425 and 1420 and well 1415 to dilute first-stage PCR product for second-stage PCR. Channel 1485 is then opened so that the second-stage PCR mix can be transferred into the second-stage PCR array 1430. Thermocycling for second-stage PCR in array 1430 may be accomplished by translating the heater assembly, by use of a Peltier, or by other means as previously described.

When fluorescent detection is desired, an optical array (see e.g., camera systems 1250 and 1325 of FIGS. 12A and 13A) may be provided. An optical array may include a light source, illustratively a filtered LED light source, filtered white light, or illumination, and a camera. The camera illustratively has a plurality of photodetectors each corresponding to a second-stage well in array 1430 of pouch 1400. Alternatively, the camera may take images that contain all of the second-stage wells, and the image may be divided into separate fields corresponding to each of the second-stage wells. Depending on the configuration, the optical array may be stationary, or the optical array may be placed on movers attached to one or more motors and moved to obtain signals from each individual second-stage well. It is understood that other arrangements are possible.

Example 1: High Density PCR

In one example, it is known that standard commercial immunofluorescence assays for the common respiratory viruses can detect seven viruses: adenovirus, PIV1, PIV2, PIV3, RSV, Influenza A, and Influenza B. A more complete panel illustratively would include assays for other viruses including: coronavirus, human metapneumovirus, rhinovirus, and non-HRV enterovirus. For highly variable viruses such as Adenovirus or HRV, it is desirable to use multiple primers to target all of the branches of the virus' lineage (illustratively 4 outer and 4 inner primer sets respectively). For other viruses such as coronavirus, there are 4 distinct lineages (229E, NL63, OC43, HKU1) that do not vary from one season to another, but they have diverged sufficiently enough that separate primer sets are required. The FilmArray® Respiratory Panel (BioFire Diagnostics, LLC of Salt Lake City, UT) includes Adenovirus, Coronavirus HKU1, Coronavirus NL63, Coronavirus 229E, Coronavirus OC43, Human Metapneumovirus, Human Rhinovirus/Enterovirus, Influenza A, Influenza A/H1, Influenza A/H3, Influenza A/H1-2009, Influenza B, Parainfluenza Virus 1, Parainfluenza Virus 2, Parainfluenza Virus 3, Parainfluenza Virus 4, and Respiratory Syncytial Virus. In addition to these viruses, the FilmArray® Respiratory Panel includes three bacteria: *Bordetella pertussis, Chlamydophila pneumoniae*, and *Mycoplasma pneumoniae*. The high density array 581 is able to accommodate such a panel in a single pouch 510. Other panels are available for the FilmArray®, each assaying for a full panel of pathogens. Other panels using pouch 510 and high density array 581 are possible.

Example 2: Fast PCR with Reduced Volume

Sample volume reduction along with cycle time reduction was performed in an instrument and pouch similar to those shown in FIGS. 1-4, with a single Peltier functioning as heaters 886 and 887, to drive thermocycling of both of blisters 548 and 564 simultaneously. In this example, the Peltier was thermocycled as fast as possible unless otherwise indicated, approximately 12° C./sec in heating and 9° C./sec in cooling. In this example, the instrument and pouch were operated to provide a 140 μl volume of a sample that contained a PCR mixture including synthetic templates and primers for amplifying the synthetic templates in blister 546. All reactions in Example 2 were performed either using this synthetic mixture or a test pouch 580 that included actual assays for organisms. When the test pouch is used, a mixture of organisms is inserted in the pouch. After 6 cycles of PCR cycling with an annealing/extension hold of 15 seconds and a denature hold of 4 seconds, the 140 μl volume in blister 546 was reduced to 70 μl by opening channel 552, followed by partial compression of bladders 848 and 864, and then closing channel 552 so that blister 548 contained 70 μl of the sample, and then the annealing/extension and denature hold times were reduced to less than one second each for an additional 17 cycles. However, initial tests provided poor results.

Figure 15:
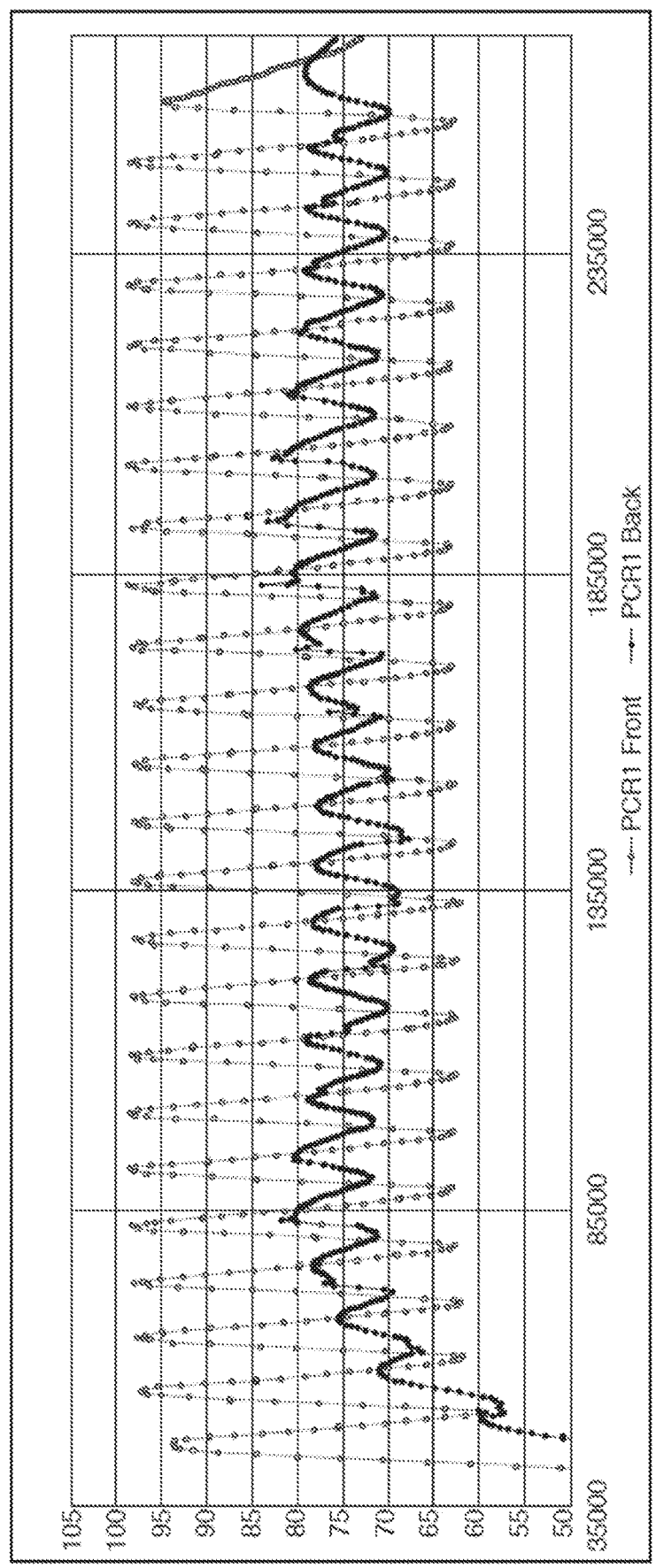
FIG. 15 shows thermocouple data recorded from the heater side (open circles) and the non-heater side (filled circles) of a first-stage amplification reaction in a pouch of FIG. 1 during fast cycling with full volume (~140 µL).

To study the temperature changes during first-stage PCR, thermocouples were provided on the heater side and the non-heater side of blister 564, while first-stage PCR was performed in blisters 548 and 564. FIG. 15 shows the results of the heater side (open circles) and the non-heater side (filled circles) during a typical run, wherein the sample having a volume of 140 μL split across blisters 548 and 564 and channel 553 was thermocycled between 98° C. and 60° C., with 0 second holds at each set point temperature. With the standard volume of blisters 548 and 564 and standard fixed cycling parameters, reaction temperatures in these blisters can take several cycles to normalize, and it is believed that PCR efficiency is very low during these early cycles. Since these initial cycles are not at optimum temperature, without being bound to theory, it is believed that sample volume reduction with faster cycle times after a few cycles was not effective because blisters 548 and 564 were not up to ideal temperature until the third or fourth cycle, with poor amplification occurring prior to sample volume reduction. If amplification efficiency is poor prior to sample volume reduction, it is believed that there may not have been enough template present for the amplification in subsequent cycles, and, thus, may not have provided sufficient template for second-stage amplification.

To mitigate the lag during the first few cycles and to address the slower kinetics with low template concentrations, higher denaturation temperatures and longer denaturation holds were used prior to sample volume reduction. While illustratively, higher denaturation temperatures and longer denaturation holds were used to equilibrate temperature within the instrument, it was believed that these reaction parameters could be effective to help overcome potential issues relating to reaction kinetics, such as starting with long genomic fragments in low abundance relative to inhibitors and the presence of other competing genomic fragments. Accordingly, the first six cycles (Steps A and B of Table 1 below) of first-stage PCR were performed with the full volume of 140 µL. The first cycle (Step A) also had an extended denaturation hold of 10 seconds to aid in normalizing the reaction temperature. While this extended hold was done during the first cycle, it is believed that such a hold at or near the denaturation temperature could be performed immediately prior to the first cycle. Because the primary goal of sample volume reduction methods was to decrease overall PCR time, only the first cycle had this extended denaturation hold of 10 seconds, while cycles 2-6 (Step B) had an extended denaturation hold of 4 seconds. However, because the first cycle denaturation hold was so long, the temperature was kept below 100° C. to reduce chances of inactivating the polymerase, while cycles 2-6 went to 100° C. but for shorter periods of time. It was believed that this high temperature for only 4 seconds would not substantially inactivate the polymerase. After the sixth cycle, to speed up thermocycling, the volume in blisters 548 and 564 was reduced by half (Step C), to about 70 µL, and then thermocycled as fast as the system would allow, with one second annealing and denaturation holds. 17 cycles were performed with reduced volume and concomitant reduced thermal mass (Step D). The following cycling parameters were used:

TABLE 1

| Step | Cycle | Denaturation Temp (° C.) | Denaturation Hold (sec) | Annealing Temp (° C.) | Annealing Hold (sec) |
|---|---|---|---|---|---|
| A | 1 | 99 | 10 | 55 | 1 |
| B | 2-6 | 100 | 4 | 55 | 1 |
| C |  | volume reduction |  |  |  |
| D | 7-23 | 98 | 1 | 55 | 1 |

Good amplification results were obtained by the thermocycling protocol shown in Table 1, with results similar to those obtained with longer cycle times and no sample volume reduction. In this illustrative protocol, no additional reaction components were added during steps A-D.

For Step A (the slowest cycle), depending on the system used, it was believed that preheating of the amplification zone for at least one slow hot cycle with a higher denaturation temperature and a longer denaturation hold was needed to bring the PCR sample up to appropriate temperature. Since it is understood that more slow, hot cycles are helpful in obtaining good amplification efficiency in PCR, it is believed that additional slow, hot cycles could be used to increase the overall reaction time.

It is believed that first-stage PCR can often start with a sample provided at 54° C. when first-stage PCR follows a reverse transcription step or 50-60° C. when the sample prep protocol uses heated elution from silica capture, and the sample is essentially at room temperature when there is no reverse transcription step. Accordingly, in the illustrative FilmArray system with a 140 µL sample, though, it was found that a first cycle denaturation hold of at least 4 seconds heats the system sufficiently to obtain good efficiency in the early cycles, with 7-10 seconds providing better amplification efficiency, and longer than 10 seconds providing no significant additional benefit. However, the length of the first cycle hold depends on the thermodynamics of the instrument, amplification container used, the temperature of the instrument (which may depend on the number of runs immediately preceding the current reaction) and the temperature of the sample immediately prior to the first cycle. It is believed that the length of the first cycle hold may be dynamically determined based on these factors. It is believed that a first-stage reaction according to Table 1 with an extra cycle in Step A, and 4 cycles in Step B (instead of the 5 cycles show) is not expected to show significantly improved results and adds about 6 seconds to the reaction time. It is also believed that in protocols where a reverse transcription stage is used prior to first-stage PCR and the reverse transcription hold is at or near the annealing temperature of first-stage PCR, Step A may be omitted or the hold time may be reduced. In such a protocol, it may be desirable to add cycles to Step B.

The denaturation temperature for the slow hot cycles illustratively were at least one degree hotter than the denaturation temperature for the subsequent cycles. To gain maximum efficiency, ideally the heater temperature should be as hot as possible, illustratively 95-105° C., without substantially damaging the polymerase or other reaction components. In a closed system such as the systems described herein, vapor from the reaction mixture was not a contamination concern, but with open systems, one may need to keep the reaction below 100° C. to avoid contamination from vapor.

The number of slow hot cycles needed to obtain maximum efficiency with minimum cycle time was studied. A total of 3, 6, 9, or 10 slow hot cycles (Step B) were evaluated prior to volume reduction. In the illustrative FilmArray system without preheating the instrument, it was found that 3 slow hot cycles were needed to get decent amplification, with 6 slow hot cycles providing better results. Amplification was not improved significantly with 9 or 10 slow hot cycles, and these protocols took additional time. To maximize amplification efficiency and overall reaction speed, it is believed that 2-10 slow hot cycles are good, illustratively 3-8 slow hot cycles, or 4-7 slow hot cycles, or 5-6 slow cycles, depending on the system used and temperature of the reaction mixture prior to amplification. Optional mixing during temperature cycling, illustratively by alternatingly adjusting the pressure of bladders 848 and 864, accordingly may be used to increase temperature uniformity within the first-stage PCR mixture.

As discussed above, multiple volume reduction steps were used. In the illustrative FilmArray system, Steps A-C, as shown in Table 1 were performed. Subsequently, 6 cycles of Step B were performed, followed by another reduction of volume to about 35 µL, followed by 17 cycles of Step D. In another example, 6 cycles of Step B were performed, followed by a 50% volume reduction and 3 additional cycles of Step B, and another volume reduction down to the void volume (to about 15-20 µL) and 14 cycles of Step D. In another example, a subsequent reduction compressed blisters 548 and 564 to their void volume (about 15-20 µL) followed by 17 cycles of Step D. No significant improvement in amplification efficiency was seen with either of these examples. However, it is noted that all of the steps in Table 1 are performed at the fastest ramp rates of the Peltiers used. In other systems, particularly such as those shown in FIGS. 6-9 and 12-14, with fixed temperature zones, it was believed that it may be possible to thermocycle faster subsequent to these additional volume reductions. It is also believed that additional volume reductions may be beneficial with faster ramp rates.

In any of these examples, the volume of blisters 548 and 564 may be reduced sufficiently such that thermocycling may proceed in only one of those blisters, and only one of heaters 886 and 887 need be used for Step D, thereby reducing total energy consumption.

Another illustrative embodiment used the following cycling parameters:

TABLE 2

| Step | Cycle | Denaturation Temp (° C.) | Denaturation Hold (sec) | Annealing Temp (° C.) | Annealing Hold (sec) |
|---|---|---|---|---|---|
| A | 1 | 99 | 10 | 53 | 1 |
| B | 2-6 | 100 | 4 | 51 | 2 |
| C |  |  | volume reduction |  |  |
| D | 7-26 | 101 | 1 | 49 | 1 |

This protocol maximized PCR efficiency and speed while balancing the constraints of temperature and volume in denaturation holds and denaturation temperatures similar to the protocol illustrated in Table 1. However, this protocol also balanced PCR efficiency and speed in altering the annealing temperatures and holds, where a longer annealing hold in Step B was balanced with a higher annealing temperature to promote annealing/extension of desired products when template copy number is at its lowest point (or to facilitate amplification of longer templates). Once a product is subsequently enriched or volume is reduced allowing the reaction to equilibrate faster, or both, the annealing parameters (hold and/or temperature) were changed to drive the reaction faster and/or more efficiently. Such protocols also balanced the need to reduce non-specific amplification by using more stringent conditions in the first few cycles, and then lowering the annealing temperatures in later cycles where the shorter holds at the annealing temperature reduced the risk of generating non-specific product.

In some embodiments, as in Table 2, subsequent to volume reduction, denaturation hold times were reduced. In other embodiments, subsequent to volume reduction, denaturation temperature may be reduced to a temperature at or just above the denaturation temperature of the amplicon. In other embodiments, both may be reduced, as desired for the specific reaction parameters.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and for purposes of illustrating the invention, it will be apparent to those skilled in the art that various changes in the methods and apparatus disclosed herein may be made without departing from the scope of the invention, which is defined in the appended claims. All changes which come within the meaning and range of equivalency of the claims are to be embraced within their scope.

What is claimed is:

1. A method for performing polymerase chain reaction (PCR), comprising
thermocycling a PCR mixture having a first volume in one amplification zone of an amplification container for a first number of cycles, each of the first number of cycles comprising a first cycle time, a first annealing temperature, a first annealing hold, a first denaturation temperature, and a first denaturation hold,
reducing the volume of the PCR mixture in the same one amplification zone to a second volume, the second volume being smaller than the first volume, and
thermocycling the second volume of PCR mixture in at least a portion of the one amplification zone for a second number of cycles, each of the second number of cycles comprising a second cycle time, a second annealing temperature, a second annealing hold, a second denaturation temperature, and a second denaturation hold, the second cycle time being shorter than the first cycle time and the second denaturation temperature being lower than the first denaturation temperature after reducing the volume of the PCR mixture;
further comprising performing an initial cycle in the one amplification zone prior to thermocycling for a first number of cycles, the initial cycle comprising an initial cycle time, an initial annealing temperature, an initial denaturation temperature, and an initial denaturation hold, wherein the initial denaturation hold is longer than the first denaturation hold, and the initial denaturation temperature is lower than the first denaturation temperature.

2. The method of claim 1, wherein the first volume of PCR mixture in the one amplification zone is thermocycled in an instrument, the one amplification zone heated by one or more heaters, further comprising reducing a thermal mass of the one or more heaters contemporaneous with or subsequent to reducing the volume of the PCR mixture to the second volume.

3. The method of claim 1, further comprising forming the first volume of PCR mixture by mixing a sample comprising nucleic acids with a PCR master mix, wherein the PCR master mix is heated above the first annealing temperature prior to mixing.

4. The method of claim 1, wherein the sample is heated to at least 50° C. prior to mixing the sample with the PCR master mix.

5. The method of claim 1, wherein the one amplification zone includes two blisters and the initial cycle, thermocycling the PCR mixture having the first volume, and thermocycling the second volume of PCR mixture take place in both blisters.

6. The method of claim 1, wherein the one amplification zone includes two blisters, wherein thermocycling the first volume of PCR mixture takes place in both of the two blisters, and wherein thermocycling the second volume of PCR takes place in only one of the two blisters.

7. A method for performing polymerase chain reaction (PCR), comprising
thermocycling a PCR mixture with a first volume in one amplification zone of an amplification container for at least a first cycle, the first cycle comprising a first cycle time, a first annealing temperature, a first annealing hold, a first denaturation temperature, and a first denaturation hold,
thermocycling for a second number of cycles in the same one amplification zone, each of the second number of cycles comprising a second cycle time, a second annealing temperature, a second annealing hold, a second denaturation temperature, and a second denaturation hold, two or more of the second cycle time, the second annealing temperature, the second annealing hold, the second denaturation temperature, and the second denaturation hold differing from the corresponding first cycle time, first annealing temperature, first annealing hold, and first denaturation temperature,
reducing the volume of the PCR mixture in the same one amplification zone to a second volume, the second volume being smaller than the first volume, and
thermocycling for a third number of cycles in the same one amplification zone, each of the third number of cycles comprising a third cycle time, a third annealing temperature, a third annealing hold, a third denaturation temperature, and a third denaturation hold, two or more of the third cycle time, the third annealing temperature, the third annealing hold, the third denaturation temperature, and the third denaturation hold differing from the corresponding second cycle time, second annealing temperature, second annealing hold, and second denaturation temperature following reducing the volume of the PCR mixture.

8. The method of claim 7, wherein the third cycle time is shorter than the second cycle time.

9. The method of claim 8, wherein the third denaturation temperature is lower than the second denaturation temperature.

10. The method of claim 8, wherein the first denaturation hold is longer than the second denaturation hold.

11. The method of claim 8, wherein the second cycle time is shorter than the first cycle time.

12. The method of claim 9, wherein the second denaturation temperature is higher than the first denaturation temperature.

13. The method of claim 10, wherein the second denaturation hold is longer than the third denaturation hold.

14. The method of claim 7, wherein the first annealing temperature is substantially the same as or greater than the second annealing temperature.

15. The method of claim 14, wherein the second annealing temperature is substantially the same as or greater than the third annealing temperature.

16. The method of claim 7, wherein the first annealing hold is substantially the same or shorter than the second annealing hold.

17. The method of claim 16, wherein the second annealing hold is substantially the same or longer than the third annealing hold.

18. The method of claim 7, wherein the first cycle has a first ramp rate, the second number of cycles has a second ramp rate, and the third number of cycles has a third ramp rate, and wherein the third ramp rate is faster than the second ramp rate.

19. The method of claim 18, wherein the second ramp rate is faster than the first ramp rate.

20. The method of claim 1, wherein no additional reaction components are added to the one amplification zone after reducing the volume and prior to thermocycling the second volume of PCR mixture.

21. The method of claim 1, wherein reducing the volume of the PCR mixture is performed by expelling a portion of the PCR mixture from the one amplification zone leaving a reduced volume of the PCR mixture in the one amplification zone.

22. The method of claim 1, wherein the one amplification zone is heated by one heater.

23. The method of claim 1, wherein the one amplification zone is heated by one or more heaters.

24. A method for performing polymerase chain reaction (PCR), comprising:
    thermocycling a PCR mixture with a first volume in an amplification zone of an amplification container for at least a first cycle, the first cycle comprising a first cycle time, a first denaturation temperature, and a first denaturation hold;
    thermocycling for a second number of cycles in the amplification zone, each of the second number of cycles comprising a second cycle time, a second denaturation temperature higher than the first denaturation temperature, and a second denaturation hold shorter than the first denaturation hold;
    reducing the volume of the PCR mixture in the amplification zone to a second volume, the second volume being smaller than the first volume; and
    thermocycling for a third number of cycles in the same one amplification zone, each of the third number of cycles comprising a third cycle time, a third denaturation temperature lower than the first or the second denaturation temperatures, and a third denaturation hold shorter than the second denaturation hold.

25. The method of claim 24, wherein the at least first cycle further comprises a first annealing temperature and a first annealing hold, the second number of cycles further comprise a second annealing temperature lower than the first annealing temperature and a second annealing hold longer than first annealing hold, and the third number of cycles further comprise third annealing temperature lower than the second annealing temperature and a third annealing hold shorter than the second annealing hold.

26. The method of claim 25, wherein the third denaturation temperature is higher than the first or the second denaturation temperatures.

* * * * *